(12) United States Patent
Nagao et al.

(10) Patent No.: US 11,000,338 B2
(45) Date of Patent: May 11, 2021

(54) ARM CONTROL METHOD AND ARM CONTROL DEVICE

(71) Applicant: SONY CORPORATION, Tokyo (JP)

(72) Inventors: Daisuke Nagao, Kanagawa (JP); Takara Kasai, Kanagawa (JP)

(73) Assignee: SONY CORPORATION, Tokyo (JP)

(*) Notice: Subject to any disclaimer, the term of this patent is extended or adjusted under 35 U.S.C. 154(b) by 318 days.

(21) Appl. No.: 16/087,437

(22) PCT Filed: Feb. 3, 2017

(86) PCT No.: PCT/JP2017/003901
§ 371 (c)(1),
(2) Date: Sep. 21, 2018

(87) PCT Pub. No.: WO2017/169103
PCT Pub. Date: Oct. 5, 2017

(65) Prior Publication Data
US 2019/0046283 A1    Feb. 14, 2019

(30) Foreign Application Priority Data

Mar. 30, 2016    (JP) .............................. JP2016-069472

(51) Int. Cl.
*G05B 19/04*      (2006.01)
*G05B 19/18*      (2006.01)
(Continued)

(52) U.S. Cl.
CPC .............. *A61B 34/37* (2016.02); *A61B 34/30* (2016.02); *A61B 90/25* (2016.02); *A61B 90/361* (2016.02);
(Continued)

(58) Field of Classification Search
CPC ........ A61B 2090/031; A61B 2090/064; A61B 34/30; A61B 34/37; A61B 90/361;
(Continued)

(56) References Cited

U.S. PATENT DOCUMENTS 5,667,186 A    9/1997    Luber et al.
2001/0013764 A1*    8/2001    Blunnenkranz ........ A61B 34/70
                                                                          318/568.11
(Continued)

FOREIGN PATENT DOCUMENTS

JP         7-16239 A    1/1995
JP         7-39190 A    2/1995
(Continued)

OTHER PUBLICATIONS

International Search Report dated May 16, 2017 in PCT/JP2017/003901, 2 pages.

*Primary Examiner* — Harry Y Oh
(74) *Attorney, Agent, or Firm* — Xsensus LLP

(57) ABSTRACT

An arm control method including determining, using a processor, whether or not there is an abnormality in an arm that operates by being driven by an actuator in a state in which the arm is fixed by a brake mechanism, to make it possible to determine whether or not there is an abnormality in an arm in a state in which the arm is fixed by a brake mechanism. Therefore, it is possible to more safely determine whether or not there is an abnormality in the arm. In addition, it is possible to more reliably prevent the arm from performing an abnormal operation.

15 Claims, 10 Drawing Sheets

(51) Int. Cl.
  *A61B 34/37* (2016.01)
  *B25J 19/06* (2006.01)
  *A61B 34/30* (2016.01)
  *B25J 9/16* (2006.01)
  *B25J 19/00* (2006.01)
  *B25J 9/06* (2006.01)
  *A61B 90/25* (2016.01)
  *A61B 90/00* (2016.01)
  *B25J 19/02* (2006.01)

(52) U.S. Cl.
  CPC .............. *B25J 9/06* (2013.01); *B25J 9/1674* (2013.01); *B25J 19/0004* (2013.01); *B25J 19/02* (2013.01); *B25J 19/06* (2013.01); *A61B 2090/031* (2016.02); *A61B 2090/064* (2016.02)

(58) Field of Classification Search
  CPC . A61B 90/25; B25J 19/02; B25J 19/06; B25J 19/00; B25J 19/0004; B25J 9/06; B25J 9/1674
  See application file for complete search history.

(56) References Cited

U.S. PATENT DOCUMENTS

| | | | | |
|---|---|---|---|---|
| 2001/0020200 A1* | 9/2001 | Das | .................. | A61B 34/30 700/260 |
| 2008/0294285 A1* | 11/2008 | Shoham | .............. | B25J 17/0266 700/245 |
| 2011/0257785 A1* | 10/2011 | Nihei | ..................... | B25J 9/1674 700/254 |
| 2012/0150347 A1* | 6/2012 | Ohga | ..................... | B25J 9/1633 700/254 |
| 2013/0310973 A1* | 11/2013 | Tanaka | .................. | B25J 9/1643 700/245 |
| 2015/0032257 A1* | 1/2015 | Hashiguchi | ........... | B25J 9/1674 700/248 |
| 2015/0258690 A1* | 9/2015 | Naitou | ................... | G01L 5/226 700/253 |
| 2017/0007336 A1 | 1/2017 | Tsuboi et al. | | |
| 2017/0143429 A1* | 5/2017 | Richmond | ............ | G16H 20/40 |
| 2018/0242938 A1* | 8/2018 | Tanaka | .................. | A61B 6/587 |

FOREIGN PATENT DOCUMENTS

| | | |
|---|---|---|
| JP | 2001-145634 A | 5/2001 |
| JP | 2010-82309 A | 4/2010 |
| JP | 2011-88219 A | 5/2011 |
| JP | 2011/0257785 A | 11/2011 |
| JP | 2013-94452 A | 5/2013 |
| WO | WO 2015/137038 A1 | 9/2015 |

\* cited by examiner

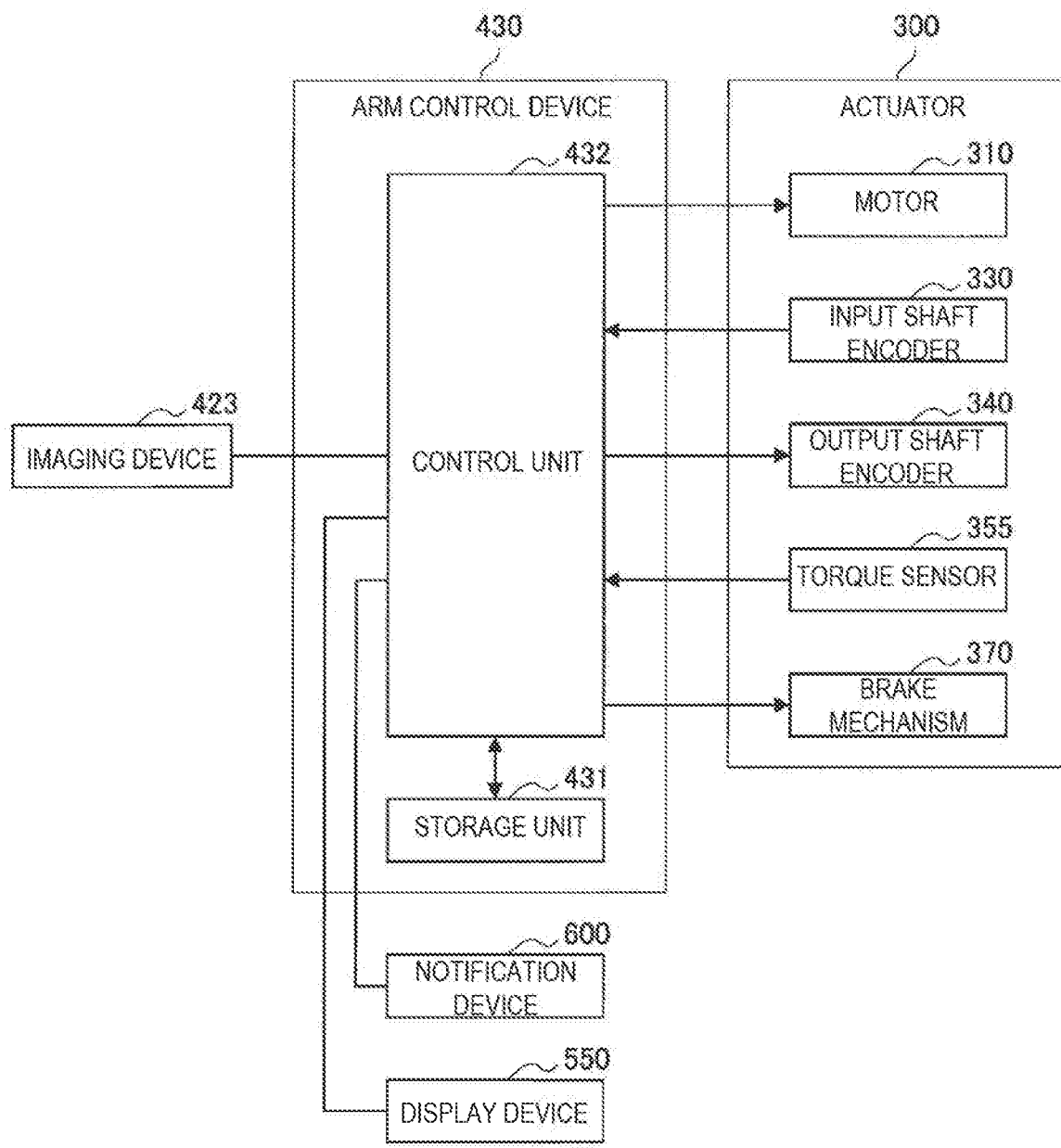

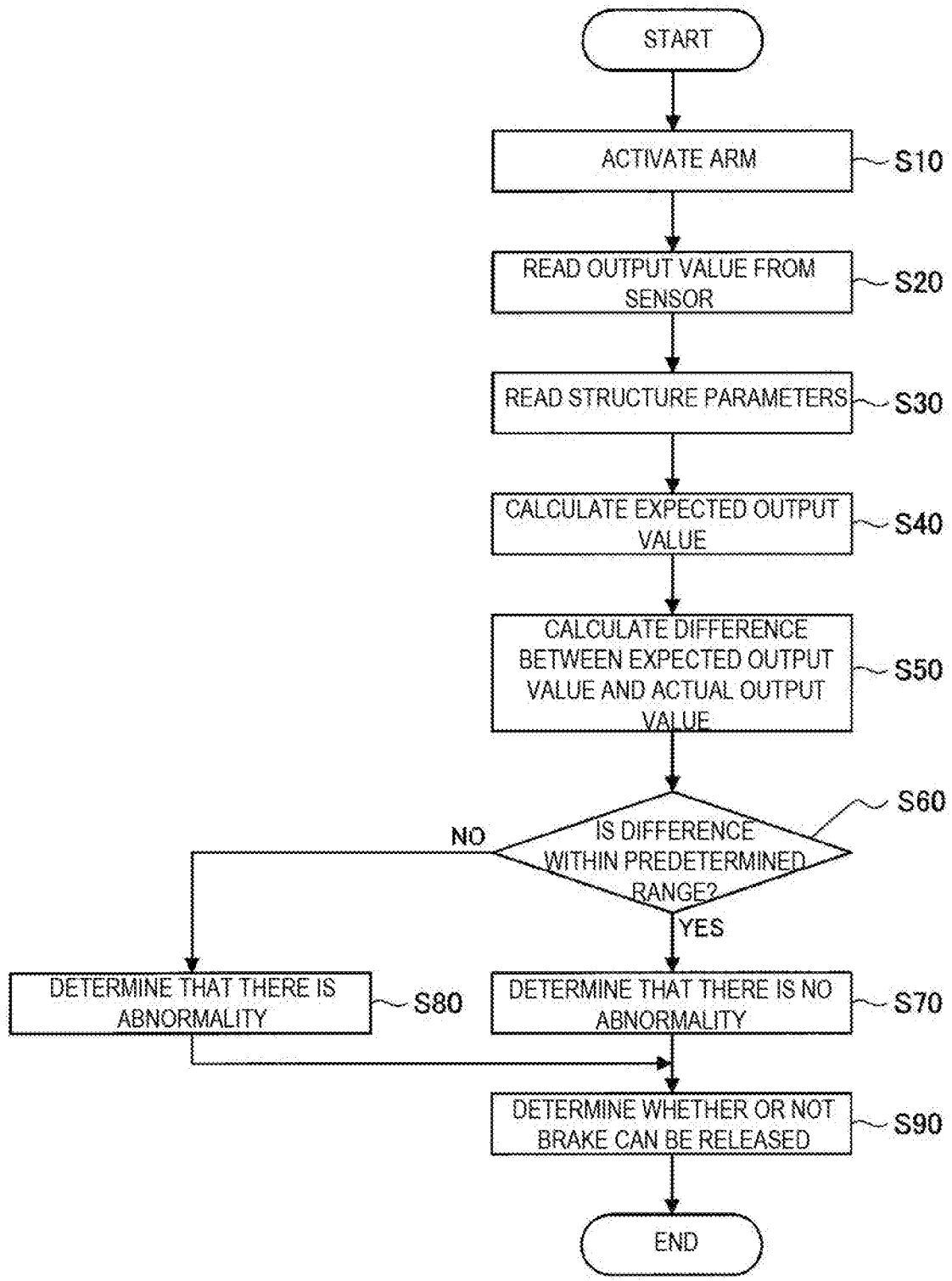

ARM CONTROL METHOD AND ARM CONTROL DEVICE

TECHNICAL FIELD

The present disclosure relates to an arm control method and an arm control device.

BACKGROUND ART

Patent literature 1 discloses a technology of determining whether or not there is an abnormality in an arm. According to the technology, the arm is caused to perform an operation of a preset operation pattern, and the result thereof is detected by a sensor. Then, it is determined whether or not there is an abnormality in the arm on the basis of the result of the detection performed by the sensor. Then, in a case in which it is determined that an abnormality has occurred in the arm, the operation of the arm is stopped.

CITATION LIST

Patent Literature

Patent Literature 1: JP 2011-88219A

SUMMARY OF INVENTION

Technical Problem

However, according to the aforementioned technology, it is not possible to determine whether or not there is an abnormality in the arm unless the arm is caused to operate in practice.

Therefore, a technology with which it is possible to determine whether or not there is an abnormality in the arm in a state in which the arm is fixed has strongly been required.

Solution to Problem

According to the present disclosure, there is provided an arm control method including determining, using a processor, whether or not there is an abnormality in an arm that operates by being driven by an actuator in a state in which the arm is fixed by a brake mechanism.

According to the present disclosure, there is provided an arm control device including a control unit that determines whether or not there is an abnormality in an arm that operates by being driven by an actuator in a state in which the arm is fixed by a brake mechanism.

Advantageous Effects of Invention

According to the present disclosure, it is possible to determine whether or not there is an abnormality in the arm in a state in which the arm is fixed as described above. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 6 is a functional block diagram of a control device and the actuator.

FIG. 7 is a flowchart illustrating a procedure for processing performed by the control device.

DESCRIPTION OF EMBODIMENTS

Figure 1:
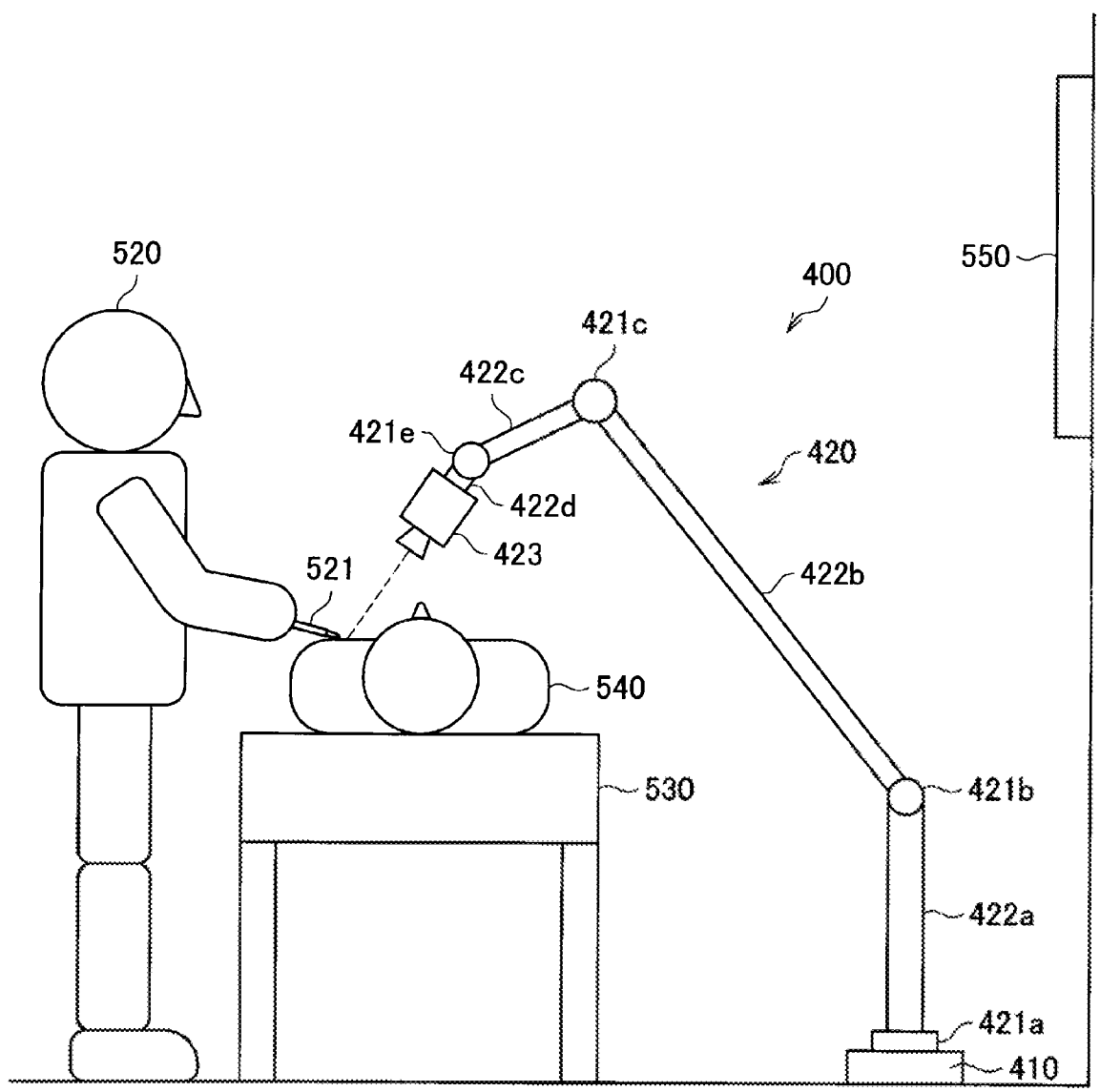
FIG. 1 is an outline diagram illustrating a situation of surgery using an arm device according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be given in the following order.
1. Outline of embodiment
2. Detailed configuration of arm device
2-1. Overall configuration
2-2. Configuration of actuator
2-3. Configuration of brake mechanism
3. Configuration of arm control device
4. Abnormality determination processing performed by arm control device
5. Modification examples of abnormality determination processing

1. Outline of Embodiment

Figure 2:
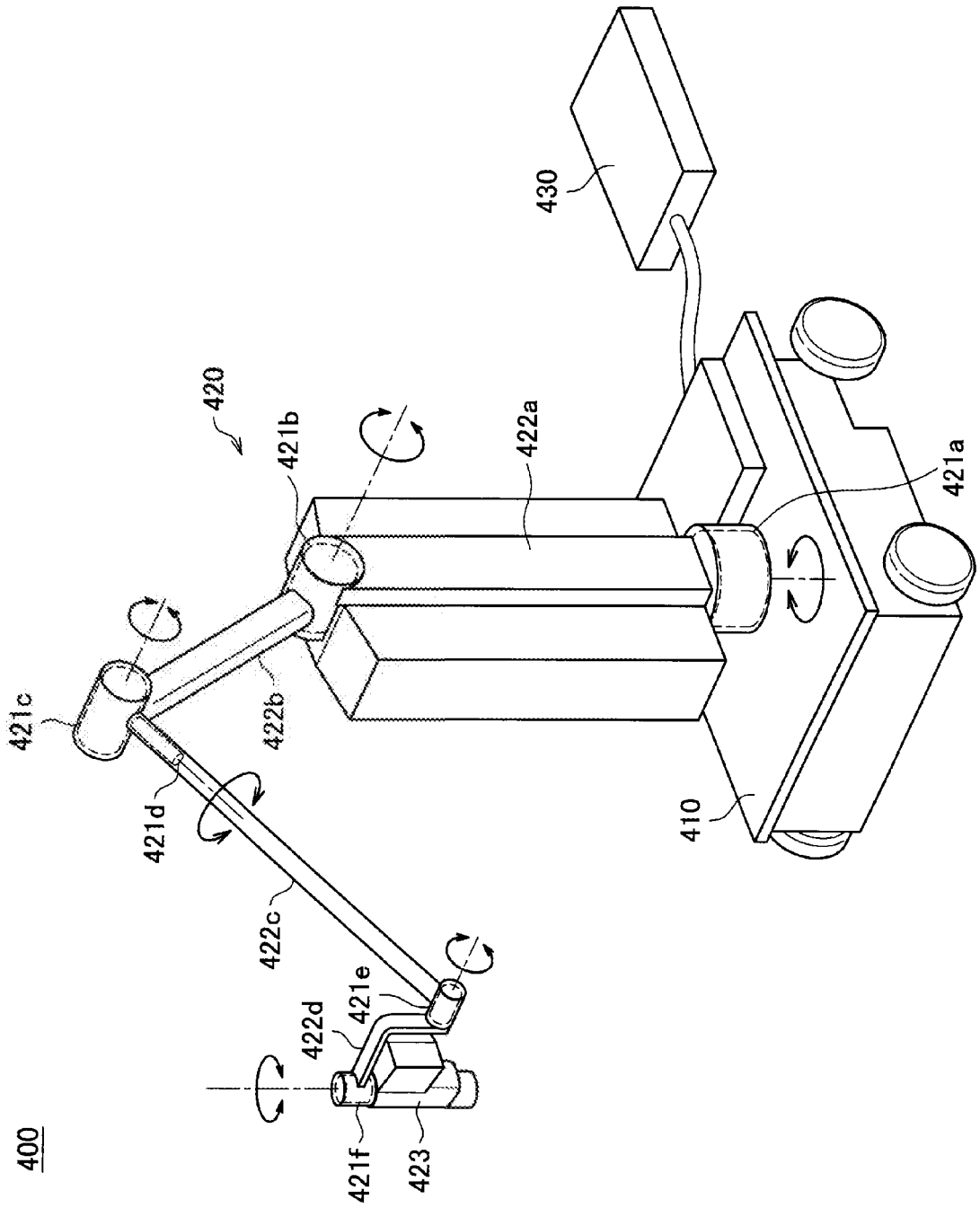
FIG. 2 is a perspective view illustrating an overall configuration of the arm device according to the embodiment.

First, an outline of an embodiment will be described on the basis of FIGS. 1 and 2. FIG. 1 illustrates an example in which an arm device 400 is used for a medical purpose, specifically for surgery as an application example of the arm device 400 according to the embodiment. FIG. 2 is a perspective view illustrating an overall configuration of the arm device. Note that the arm device 400 is illustrated in a simple manner in FIG. 1. It is a matter of course that the arm device 400 according to the embodiment may be applied to other fields (for example, fields of various industries (automobiles and the like), agriculture, and the like). As an application to the field of industry, an application to an arm that is included in a manufacturing assembly line is exemplified. It is a matter of course that the embodiment may be applied to other purposes.

As illustrated in FIG. 1, a surgeon 520 uses a treatment tool 521 for surgery, such as a scalpel, a pair of tweezers, or a pair of forceps, for example, and carries out surgery on a patient 540 who is on a surgical table 530. The arm device 400 according to the embodiment is provided next to the surgical table 530. The arm device 400 includes a base portion 410 as a platform and an arm 420 that extends from the base portion 410. In addition, an arm control device 430 (see FIG. 2) that controls operations of the arm device 400 is coupled to the arm device 400.

The arm 420 has a plurality of joint portions 421a to 421f, a plurality of links 422a to 422d that couple the joint portions 421a to 421, and an imaging device 423 that is provided at a tip end of the arm 420. Actuators 300 illustrated in FIG. 3, which will be described later, are provided at the joint portions 421a to 421f, and the joint portion 421a to 421f can rotate relative to predetermined rotation shafts by being driven by the actuators 300. The rotation angles of the respective joint portions 421a to 421c are controlled, and driving of the arm 420 is controlled, by the driving of the actuators 300 being controlled by the aforementioned arm control device 430. That is, the arm 420 operates by being driven by the actuators 300.

Note that it is a matter of course that the number and arrangement of the joint portions 421a to 421f and the links 422a to 422d and the rotation directions of the joint portions 421a to 421f are not limited to the example illustrated in FIGS. 1 and 2. In one example, the arm 420 can be suitably configured to have a degree of freedom that is equal to or greater than six degrees of freedom. In this manner, it is possible to cause the imaging device 423 to freely move within a movable range of the arm 420. FIG. 2 illustrates an example of the arm 420 that has six degrees of freedom.

The imaging device 423 is a device that allows observation of a surgical site of the patient 540 and is a camera or the like capable of capturing a moving image and/or a stationary image of an object to be imaged, for example. The imaging device 423 can be a so-called video-type microscope that appropriately enlarges and electronically images the object to be imaged. As other examples of the imaging device, an endoscope, an optical microscope, and the like can be listed, for example. The arm device with these imaging devices for allowing observation of the surgical site of the patient 540 provided at the tip end of the arm 420 will also be referred to as an observation device in this specification.

When surgery is performed, the positions and the postures of the arm 420 and the imaging device 423 are controlled by the arm device 400 such that the imaging device 423 provided at the tip end of the arm 420 images the surgical site of the patient 540 as illustrated in FIG. 1. In a surgical room, a display device 550 is installed at a position at which the display device 550 faces the surgeon 520, and the image of the surgical site captured by the imaging device 423 is displayed on the display device 550. The surgeon 520 performs various kinds of treatment while observing the image of the surgical site displayed on the display device 550.

Note that equipment other than the imaging device such as the imaging device 423, for example, various medical tools or the like may be provided at the tip end of the arm 420. Examples of the medical tools can include various treatment tools such as a pair of forceps or a retractor as well as the aforementioned imaging device. Although many medical staff members are conventionally required for surgery since operations of these medical tools are manually performed, it is possible to perform surgery with less persons by performing the operations of these medical tools using the arm device 400.

The situation of the surgery in which the arm device 400 according to the embodiment is used has been described above with reference to FIG. 1. Although the arm device 400 is used for the surgery in the example illustrated in FIG. 1, the arm device 400 may be used for the purpose of inspection in a case in which an inspection unit such as an endoscope is provided as the tip-end unit, for example.

In this manner, the arm device 400 used for the surgery is installed in the vicinity of the surgeon 520 and the patient 540 in many cases. Therefore, it is necessary not to allow the arm 420 to perform abnormal operations, for example, operations that the surgeon 520 does not expect. This is because there is a possibility that the arm 420 is brought into contact with the surgeon 520 or the patient in a case in which the arm 420 performs abnormal operations. In particular, there is a case in which a heavy object such as the imaging device 423 is provided at the tip end of the arm 420. In addition, there is also a case in which a medical tool with a sharp portion is provided at the tip end of the arm 420. In these cases, it is necessary to more reliably prevent the tip end of the arm 420 from being brought into contact with the surgeon 520 and the patient 540. Here, malfunction of the motor 310 in the actuators 300, malfunction of sensors (specifically, a torque sensor 355, an input shaft encoder 330, and an output shaft encoder 340, which will be described later), and the like are assumed, for example, as abnormalities that may occur in the arm device 400.

Thus, the arm control device 430 determines whether or not there is an abnormality in the arm 420 in a state in which the arm 420 is fixed by brake mechanisms 370 (see FIG. 3 and the like) when the arm 420 is activated, in the embodiment. In this manner, it is possible to detect an abnormality in the arm 420 without allowing the arm 420 to perform an abnormal operation even in a case in which there is an abnormality in the arm 420. That is, the arm control device 430 can more safely determine whether or not there is an abnormality in the arm 420.

More specifically, it is determined whether or not there is an abnormality in the sensors in a state in which the arm 420 is fixed by the brake mechanisms 370. In this manner, it is possible to detect the abnormality in the sensors in the state in which the arm 420 is fixed by the brake mechanisms 370 in a case in which both the motor 310 and the sensor have experienced malfunction, for example. Therefore, it is possible to detect the abnormality in the sensors without allowing the arm 420 to perform an abnormal operation immediately after the arm 420 is activated, for example. Further, the brake mechanisms 370 are not released in the embodiment. Similar processing is also performed in a case in which only a sensor has experienced a malfunction. This is because there is a possibility that the arm 420 may perform an abnormal operation even if the motor 310 is operating normally. As such a case, a case in which an abnormal operation signal is provided to the actuators 300 or the like may be assumed, for example. In this case, there is a possibility that an abnormal operation of the arm 420 may not be able to be detected if the sensor has experienced a malfunction. However, it is possible not to allow the arm 420 to operate with an abnormal operation since the brake mechanisms 370 are not released in the embodiment.

Meanwhile, the brake mechanisms 370 are released in a case in which the sensors are operating normally according to the embodiment. Note that a case in which the sensors are operating normally while there is an abnormality in the motor 310 may be assumed. However, it is possible to immediately stop the arm 420 in a case in which the arm 420 is about to perform an abnormal operation since the sensors are operating normally. In this case, an abnormal value is output from a sensor.

Therefore, it is possible to determine whether or not there is an abnormality in the arm 420 in the state in which the arm 420 is fixed and thus to more reliably prevent the arm 420 from performing an abnormal operation according to the embodiment.

Note that it is important to secure safety of the arm 420 even in a case in which the arm 420 is used for a purpose other than medical purposes, for example, in a case in which the arm 420 is used as an industrial arm. Safety is significantly important especially in a case in which a person is present in the surroundings of the arm 420. Therefore, the embodiment can be suitably applied to a field other than medical use. Hereinafter, details of the embodiment will be described with reference to an example in which the arm 420 is applied to medical use.

2. Detailed Configuration of Arm Device (2-1. Overall Configuration)

An overall configuration of the arm device according to the embodiment will be described with reference to FIG. 2. FIG. 2 is a diagram illustrating the overall configuration of the arm device according to the embodiment.

Referring to FIG. 2, the arm device 400 includes a base portion 410, an arm 420, and an arm control device 430. The arm device 400 is an arm device that can be suitably applied to surgery, inspection, and the like similarly to the arm device 400 illustrated in FIG. 1 as described above.

The base portion 410 is a platform of the arm device 400, and the arm 420 extends from the base portion 410. Casters are provided on the base portion 410, and the arm device 400 comes into contact with a floor surface via the casters and is configured to be movable on the floor surface using the casters. However, the configuration of the arm device 400 according to the embodiment is not limited to such an example, and the arm device 400 may be configured such that the base portion 410 is not provided and the arm 420 is attached directly to a ceiling or a wall surface of a surgery room, for example. In a case in which the arm 420 is attached to the ceiling, for example, the arm device 400 is configured such that the arm 420 is suspended from the ceiling.

The arm 420 has the plurality of joint portions 421a to 421f, a plurality of links 422a to 422d that couple the joint portions 421a to 421f, and the imaging device 423 that is provided at the tip end of the arm 420.

The links 422a to 422d are bar-like members. The link 422a couples the joint portion 421a and the joint portion 421b. Here, the joint portion 421a is provided on the base portion 410. In addition, the link 422b couples the joint portion 421b and the joint portion 421c. The link 422c couples the joint portion 421c and the joint portion 421e. Here, the joint portion 421d is incorporated in the link 422c. In addition, the link 422d couples the joint portion 421e and the joint portion 421f. Further, the imaging device 423 is coupled to the tip end of the arm 420, that is, the joint portion 421f. In this manner, the plurality of joint portions 421a to 421f are coupled to each other by the plurality of links 422a to 422d by using the base portion 410 as a support point.

The imaging device 423 is an example of an imaging device for allowing observation of a surgical site and is a camera or the like capable of capturing a moving image and/or a stationary image of an object to be imaged, for example. The image of the surgical site of the patient captured by the imaging device 423 is displayed on the display device 550 provided in the surgery room, for example, in an appropriately enlarged manner, and the surgeon 520 conducts surgery while observing the image of the surgical site of the patient displayed on the display device 550. The imaging device 423 can be a so-called video-type microscope. In this manner, the arm device 400 can be an observation device with the imaging device 423 attached to the tip end of the arm 420. As described above, an endoscope, or an optical microscope, for example can be provided in other cases as the imaging device 423.

However, equipment other than the imaging device 423 may be connected to the tip end of the arm 420. For example, various medical tools may be attached to the tip end of the arm 420. As the medical tools, various treatment tools such as a pair of forceps, or a retractor, for example, may be exemplified. A light source for an endoscope or a microscope or a surgical microscope used for sealing blood vessels, for example, may be connected to the tip end of the arm 420.

The actuators 300 illustrated in FIG. 3, which will be described later, are provided at the joint portions 421a to 421f, and the joint portions 421a to 421f can rotate relative to predetermined rotation shafts by being driven by the actuators 300. The driving of the actuators 300 is controlled by the arm control device 430. The driving of the arm 420, such as extension and contraction (folding) of the arm 420, for example, is controlled by driving of the actuators 300 at the respective joint portions 421a to 421f being respectively controlled.

Here, the brake mechanisms 370 that release the rotation shafts of the joint portions 421a to 421f when electrical power is distributed and restrain the rotation shafts when electrical power is not distributed are provided at the actuators 300 of the respective joint portions 421a to 421f. Further, a braking force of the brake mechanisms 370 has a magnitude such that the weight of the arm 420 is supported and a posture when electrical power is not distributed is maintained. In this manner, the arm 420 can maintain the current posture even in a case in which electrical power to the arm 420 is cut off during surgery. Therefore, safety of the arm 420 is further enhanced. Here, the braking force from the brake mechanism 370 may be adjusted such that the rotation shafts can be operated using an eternal force that is equal to or greater than a predetermined value. In this manner the convenience of the arm 420 is further improved. For example, the surgeon 520 may continue surgery by manually moving the arm 420 even in a case in which electrical power to the arm 420 is cut off during surgery. Note that configurations of the actuators 300 and the brake mechanisms will be described later (2-2. Configuration of actuator) in detail. In addition, the arm control device 430 determines whether or not there is an abnormality in the arm 420 in a state in which the arm 420 is fixed by the brake mechanisms 370 in the embodiment though detailed description will be given later.

Note that the arm device 400 has the six joint portions 421a to 421f and six degrees of freedom are realized in relation to the driving of the arm 420 in the example illustrated in the drawing. It is possible to cause the imaging device 423 to freely move within a movable range of the arm 420 with the arm 420 configured to have six degrees of freedom. In this manner, it is possible to image a surgical site at various angles and distances by the imaging device 423. However, the configuration of the arm 420 is not limited to the example illustrated in the drawing, and the numbers and the arrangement of the joint portions 421a to 421f and the links 422a to 422c and the directions and the like of the driving shafts of the joint portions 421a to 421f may be appropriately set such that the arm 420 has a desired degree of freedom. However, the arm 420 can suitably be configured to have a degree of freedom that is equal to or greater than the six degrees of freedom in consideration of degrees of freedom in the position and the posture of the imaging device 423.

In addition, although the arm control device 430 is connected to the base portion 410 via a cable in the example illustrated in the drawing, a control substrate or the like that has functions similar to those of the arm control device 430 may be provided inside the base portion 410.

The outline configuration of the arm device 400 according to the embodiment has been described above with reference to FIG. 2.

(2-2. Configuration of Actuator)

Next, a configuration of the actuators provided at the respective joint portions 421a to 421f of the arm device 400 illustrated in FIG. 2 will be described with reference to FIGS. 3 and 6. FIG. 3 is an exploded perspective view illustrating a configuration example of an actuator provided at each of the joint portions 421a to 421f of the arm device 400 according to the embodiment. FIG. 6 is a functional block diagram of the arm control device 430 and the actuator 300. Note that the actuators 300 may not necessarily be provided at all the joint portions 421a to 421f. The joint portions with no actuators 300 provided serve so-called passive shafts. In contrast, the joint portions with the actuators 300 provided serve as active shafts. However, it is preferable that the brake mechanisms 370 are also provided at the joint portions that serve as the passive shafts. This is for suppressing an abnormal operation when the electric power is not distributed.

Figure 3:
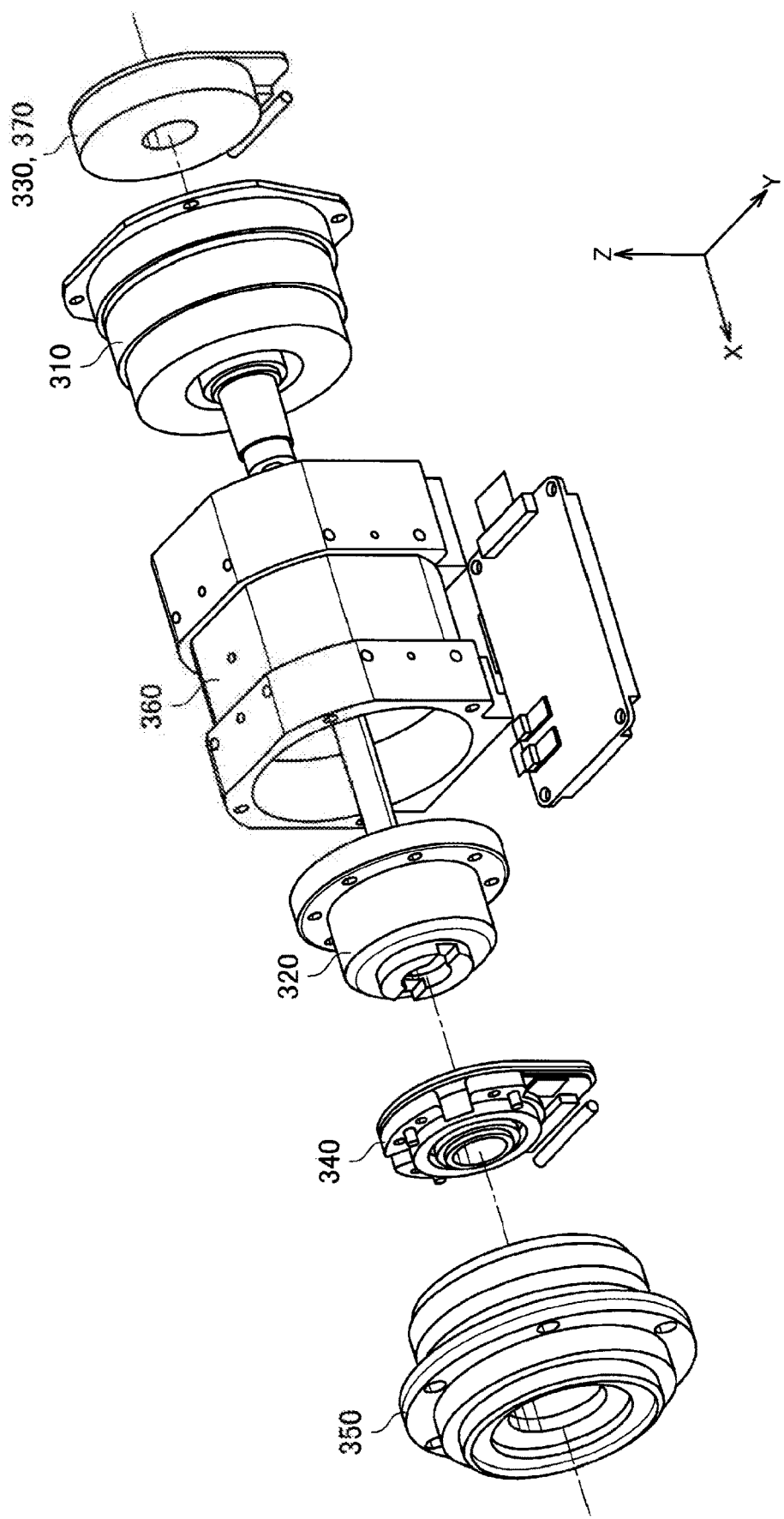
FIG. 3 is an exploded perspective view illustrating a configuration example of an actuator provided at each joint portion in the arm device according to the embodiment.

Referring to FIGS. 3 and 6, the actuator 300 includes the motor 310, a decelerator 320, the input shaft encoder 330, the output shaft encoder 340, the output shaft 350, the torque sensor 355, a housing 360, and the brake mechanism 370. The actuator 300 is adapted such that another member in the following stage is driven by rotation of the rotation shaft of the motor 310 being decelerated at a predetermined deceleration ratio by the decelerator 320 and being delivered to above another member via the output shaft 350. Here, above another member is a link (or the imaging device) connected directly to the joint portion on the tip end side of the arm 420. For example, the actuator 300 provided inside the joint portion 421a causes the link 422a to be driven.

Note that the direction of the rotation shaft of the actuator will also be referred to as an x-axis direction in the following description. In addition, two directions that perpendicularly intersect one another in a plane vertical to the x-axis direction will also be referred to as a y-axis direction and a z-axis direction, respectively.

The housing 360 has a substantially cylindrical shape, and the respective components are stored therein. The actuator 300 is assembled in each of the joint portions 421a to 421f of the aforementioned arm device 400 in a state in which the respective components are stored in the housing 360.

The motor 310 is a drive mechanism that causes drive force by rotating the rotation shaft at a rotation speed corresponding to a predetermined command value (current value) in a case in which the command value is provided. The command value is sent from the arm control device 430. As the motor 310, a brushless motor, for example, is used.

However, the embodiment is not limited to such an example, and various known motors may be used as the motor 310.

The decelerator 320 is coupled to the rotation shaft of the motor 310. The decelerator 320 decelerates the rotation speed of the rotation shaft of the motor 310 coupled thereto (that is, a rotation speed of the input shaft) at a predetermined deceleration ratio and delivers it to the output shaft 350. In other words, the decelerator 320 increases a torque of the input shaft of the motor 310 and delivers it to the output shaft 350. In the embodiment, the configuration of the decelerator 320 is not limited to a specific configuration, and various known decelerators may be used as the decelerator 320. However, it is preferable that a decelerator capable of highly accurately setting the deceleration ratio, such as Harmonic Drive (registered trademark), for example, be used as the decelerator 320. In addition, the deceleration ratio of the decelerator 320 can be appropriately set in accordance with the purpose of the actuator 300. In a case in which the actuators 300 are applied to the joint portions 421a to 421f of the arm device 400 as in the embodiment, for example, the decelerator 320 that has a deceleration ratio of about 1:100 can preferably be used. Note that in a case in which the motor 310 can cause a torque that is sufficient to drive the links (or the imaging device) the decelerator 320 may be omitted.

The input shaft encoder 330 detects the rotation angle of the input shaft (that is, the rotation angle of the motor 310). The output shaft encoder 340 detects the rotation angle of the output shaft 350. The arm control device 430 reads output values from these encoders. The configurations of the input shaft encoder 330 and the output shaft encoder 340 are not limited, and various known rotary encoders such as magnetic encoders or optical encoders, for example, may be used as the input shaft encoder 330 and the output shaft encoder 340. Note that any of the encoders may be omitted. In the embodiment, it is determined whether or not there is an abnormality in the respective encoders and the torque sensor 355 on the basis of the output values from these encoders.

The output shaft 350 is the link (or the imaging device) that is connected to the joint portion on the tip end side of the arm 420 as described above. Further, the output shaft 350 includes the torque sensor 355 incorporated therein. Therefore, the torque sensor 355 can detect a torque acting on the output shaft 350. Here, a torque provided from the outside of the actuator 300 to the output shaft 350 (a so-called external torque) can also be detected in addition to the torque provided from the decelerator 320, as the torque acting on the output shaft 350. Here, the external torque is a torque provided from all structural bodies (that is, the link, the joint portion, and the imaging device) that are present on the tip end side of the arm 420 beyond the joint portion at which the actuator 300 is provided.

Further, the torque sensor 355 can detect the aforementioned external torque even in a case in which the rotation shaft of the actuator 300) is fixed by the brake mechanism 370 since the torque sensor 355 is incorporated in the output shaft 350. In the embodiment, it is determined whether or not there is an abnormality in the respective encoders and the torque sensor 355 on the basis of the external torque.

Note that the installation position of the torque sensor 355 is not limited to the aforementioned installation position. That is, the torque sensor 355 may be installed at any position as long as it is possible to detect the external torque when the rotation shaft of the actuator 300 is fixed by the brake mechanism 370. For example, the torque sensor 355 may be installed between the decelerator 320 and the motor 310. In this case, an output value of the torque sensor 355 indicates a torque before the decelerator 320 increases the torque. Therefore, it is preferable that the output value of the torque sensor 355 be subjected to a correction coefficient in a case in which it is determined whether or not there is an abnormality in the torque sensor 355. The correction coefficient corresponds to the deceleration ratio of the decelerator 320. In addition, in a case in which the decelerator 320 is omitted, the torque sensor 355 may be provided at the rotation shaft of the motor.

In addition, any torque sensor 355 may be used regardless of the type thereof, in particular, as long as the aforementioned functions are realized. For example, the torque sensor 355 may be a non-contact-type torque sensor or may be a contact-type torque sensor.

The brake mechanism 370 has functions of releasing the rotation shaft of the actuator 300 when the electrical power is distributed and constraining the rotation shaft of the actuator 300 when the electrical power is not distributed. In the example illustrated in the drawing, the brake mechanism 370 is configured integrally with the input shaft encoder 330 and is configured to stop the rotation of the actuator 300 by constraining the rotation shaft (that is, the input shaft) of the motor 310.

However, the arrangement of the brake mechanism 370 is not limited to the example illustrated in the drawing, and the brake mechanism 370 may be arranged as a member separate from the input shaft encoder 330. In addition, the brake mechanism 370 may not necessarily be provided at the input shaft and may be provided at any position as long as the torque sensor 355 can detect the external torque. For example, the brake mechanism 370 may be provide between the motor 310 and the decelerator 320. Note that the torque sensor 355 is provided on the side of the output shaft 350 beyond the brake mechanism 370.

Brake force of the brake mechanism 370 is adjusted such that the weight of the arm 420 can be supported and the posture of the arm 420 can be held in a case in which electrical power supply is cut off. In this manner, it is possible to cause the arm 420 to safely stop at the time of emergency such as interruption of electric supply.

Further, the brake force of the brake mechanism 370 has preferably been adjusted such that the rotation axis can rotate in accordance with external force that is greater than a predetermined value in a case in which the external force is loaded. In this manner, it s possible to manually move the arm 420 even at the time of losing a power source and to thereby continue a surgery. Note that a specific configuration of the brake mechanism 370 will be described later (2-3. Configuration of brake mechanisms).

Note that although the brake mechanisms 370 can be provided at all the joint portions 421a to 421f in order to hold the posture of the arm 420 when the electrical power is not supplied, the adjustment of the brake force as described above may not be performed on all the brake mechanisms 370. For example, the adjustment of the brake force as described above may be performed on the brake mechanisms 370 of the actuators 300 provided at the joint portions, which can realize operations necessary to continue the surgery, from among the joint portions 421a to 421f. This is because it is sufficient that only the joint portions that can define the posture of the tip end unit from among the joint portions 421a to 421f can operate in accordance with the external force in a case in which the arm 420 is fixed due to interruption of power supply during the surgery, for example, since it is difficult to consider that the arm 420 is moved such that the position of the tip end unit is caused to significantly change after the surgery is started.

In the configuration example illustrated in FIG. 2, the adjustment of the brake force as described above may be performed only on the brake mechanisms 370 of the actuators 300 provided at the joint portions 421d to 421f that are joint portions that are provided on a further tip end side and can define the posture of the imaging device 423. In this case the brake mechanisms 370 of the actuators 300 provided at the remaining joint portions 421a to 421c may have strong brake force to more firmly fix the position and the posture of the arm 420 when the electrical power is not distributed. In this manner, it becomes easier to design the arm 420 since it is only necessary to adjust the brake force of the partial brake mechanisms 370 from among the brake mechanisms 370 provided at the arm 420 and it is not necessary to design the brake force in detail for the other brake mechanisms 370.

In addition, in a case in which the respective joint portions 421d to 421f are well balanced in terms of the configurations on the tip end side that are to be supported (that is, in a case in which the gravity centers of the configurations on the tip end side are positioned on the rotation shafts of the joint portions 421d to 421f), the brake mechanisms 370 may not necessarily be provided at the joint portions 421d to 421f. This is because the posture of the arm 420 can be held without causing the brake force at the joint portions in a case in which the configurations on the tip end side beyond a certain joint portion that forms the arm 420, which are to be supported by the joint portion, are well balanced with respective to the joint portion.

For example, the brake mechanism 370 may not necessarily be provided at the joint portion 421f in a case in which the arm 420 is configured such that the rotation shaft of the joint portion 421f that supports the imaging device 423 is the rotation shaft that is substantially parallel to an optical axis of the imaging device 423 as in the configuration example illustrated in FIG. 2. This is because there is a high possibility that the gravity center of the imaging device 423 is positioned on the rotation shaft of the joint portion 421f, that is, there is a high possibility that the imaging device 423 is well balanced with respect to the joint portion 421f in a case in which the rotation shaft of the joint portion 421f is substantially parallel to the optical axis of the imaging device 423 as described above since the imaging device 423 generally has a cylindrical shape in many cases and the gravity center thereof is positioned on the optical axis in many cases. Therefore, it is considered to be difficult that the imaging device 423 moves (rotates) due to its own weight when the power source is lost even in a case in which the brake mechanism 370 is not provided at the joint portion 421f.

However, it is preferable that the brake mechanisms 370 be provided at all the joint portions 421a to 421f from the viewpoint of determining whether or not there is an abnormality in the arm 420 without allowing the arm 420 to perform an abnormal operation.

The overall configuration of the actuator 300 according to the embodiment has been described above with reference to FIG. 3. Note that the actuator 300 may further include configurations other than the configurations illustrated in the drawing. For example, the actuator 300 may further include various members that a general actuator can have, such as a driver circuit (driver integrated circuit (IC)) that causes the motor 310 to rotate and drives the motor 310 by supplying a current to the motor 310.

(2-3. Configuration of Brake Mechanism)

Figure 4:
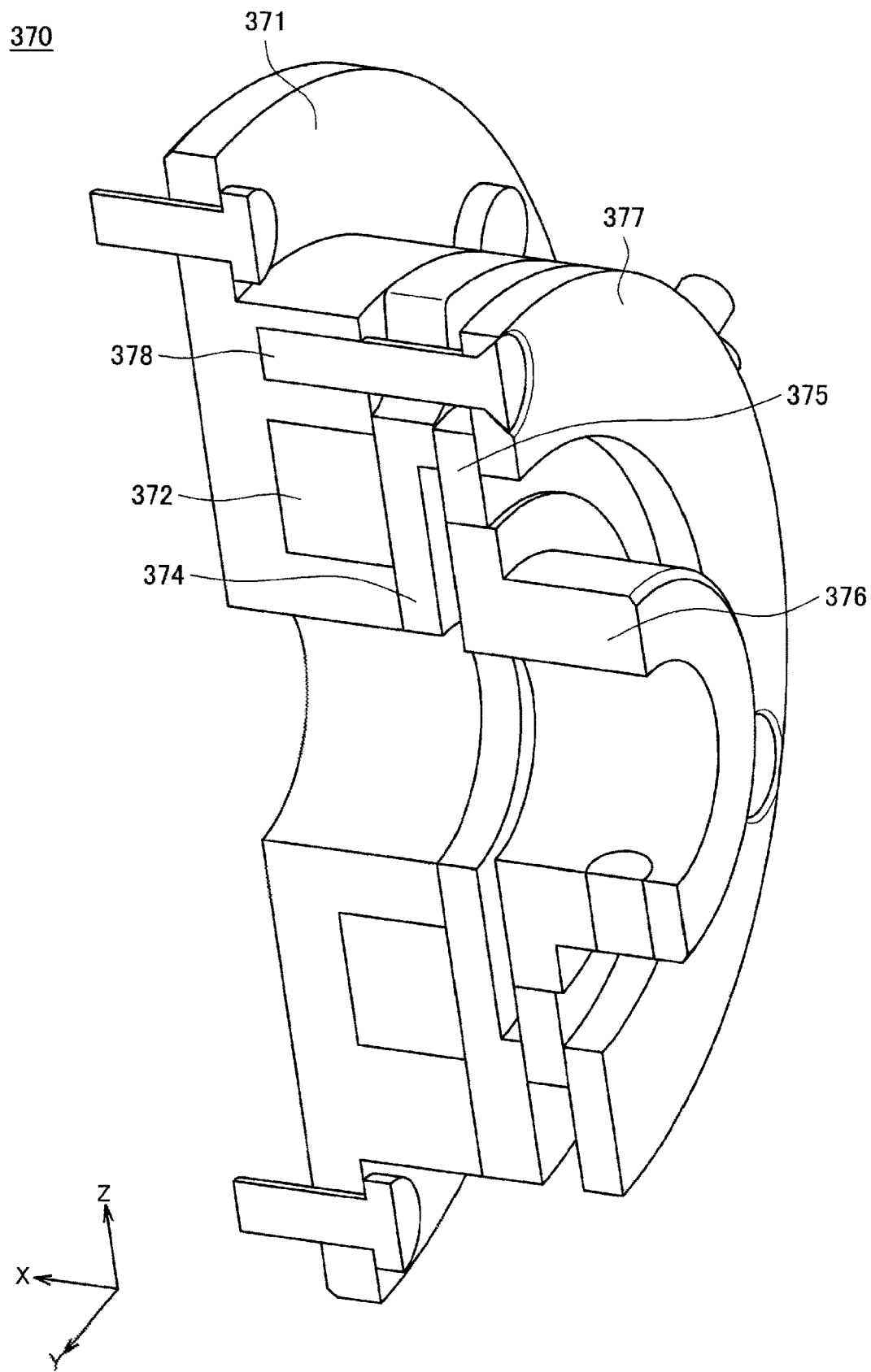
FIG. 4 is a sectional perspective view illustrating a configuration example of a brake mechanism according to the embodiment.
Figure 5A:
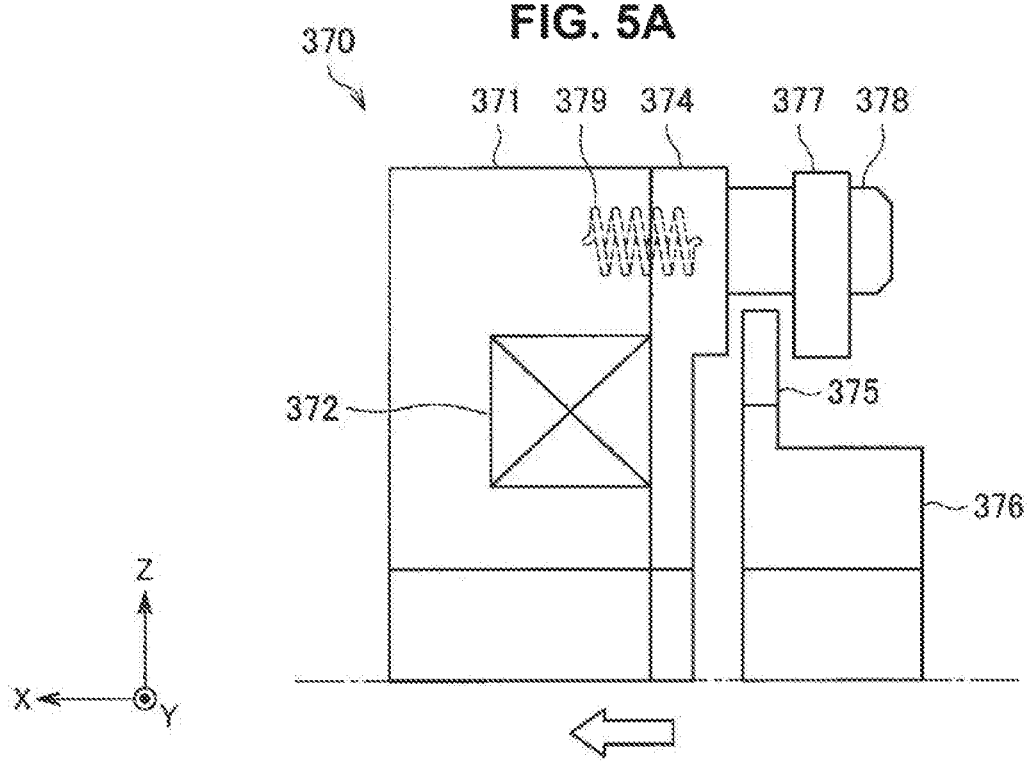
FIG. 5A is an explanatory diagram for describing operations of the brake mechanism according to the embodiment
Figure 5B:
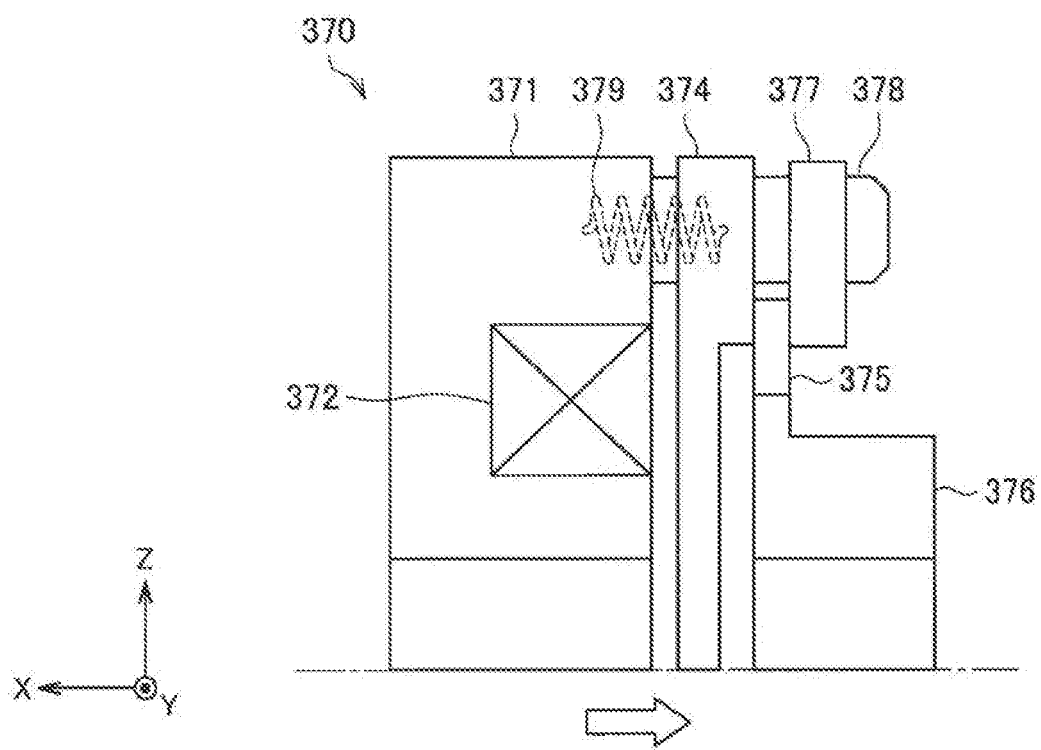
FIG. 5B is an explanatory diagram for describing operations of the brake mechanism according to the embodiment.

A configuration of the brake mechanism 370 according to the embodiment will be described in detail with reference to FIGS. 4, 5A, and 5B. FIG. 4 is a sectional perspective view illustrating the configuration of the brake mechanism 370 according to the embodiment. FIGS. 5A and 5B are explanatory diagrams for describing operations of the brake mechanism 370 according to the embodiment. Note that the brake mechanism 370 is a brake mechanism that is referred to as a so-called dry multiple-disk electromagnetic brake.

FIG. 4 illustrates a sectional perspective view in a case in which the brake mechanism 370 is cut along a plane passing through the center axis. Referring to FIG. 4, the brake mechanism 370 is configured such that a base material 371, an armature 374, and a hub 376, all of which have substantially disk shapes, overlap each other in the rotation shaft direction (x-axis direction). Opening portions are provided at substantially the center of the disk shapes of the base material 371, the armature 374, and the hub 376, and the rotation shaft of the actuator 300 (the rotation shaft of the motor 310 in the example illustrated in FIG. 3) is inserted into the opening portion.

The hub 376 is fixedly fit to the rotation shaft of the actuator 300 and rotates along with the rotation shaft of the actuator 300 in conjunction with the driving of the actuator 300. Meanwhile, the base material 371 and the armature 374 are connected to the rotation shaft of the actuator 300 via a bearing (not illustrated). In addition, the armature 374 is configured to be movable in the rotation axis direction between the base material 371 and the hub 376.

Furthermore, a disk 375 and a plate 377 with substantially annular shapes are provided at the outer circumference of the hub 376. In a region corresponding to the outer circumference of the hub 376, the armature 374, the disk 375, and the plate 377 are laminated in this order in the rotation shaft direction.

The hub 376 and the disk 375 are coupled with a spline, and the hub 376 and the disk 375 rotate integrally with the rotation shaft of the actuator 300. Meanwhile, the plate 377 is connected to the base material 3371 and the armature 374 with a bolt 378 without the hub 376 mediating therebetween. That is, only the hub 376 and the disk 375 rotate along with the rotation shaft of the actuator 300, from among the illustrated configurations in the brake mechanism 370.

A coil 372 is provided inside the base material 371. In addition, the base material 371 and the armature 374 are connected to each other with a spring (not illustrated). The armature 374 moves in the rotation axis direction by magnetic force caused by a current applied to the coil 372 or recovery force caused by the spring, and release and activation of the brake are realized.

Next, operations of the brake mechanism 370 will be described in detail with reference to FIGS. 5A and 5B. FIGS. 5A and 5B schematically illustrate only a configuration corresponding to a half with the center axis interposed in the section passing through the center axis of the brake mechanism 370 for simplification. In addition, FIGS. 5A and 6B schematically illustrate a spring 379, which is omitted in the illustration of FIG. 4.

FIG. 5A illustrates a condition of the brake mechanism 370 when the electrical power is distributed, that is, in a case in which the electrical power is supplied to the coil 372. This corresponds to a state in which the constraint of the rotation shaft of the actuator 300 by the brake mechanism 370 has been released.

The armature 374 moves in the rotation shaft direction such that the armature 374 is attracted by the base material 371 due to the magnetic force caused by the power distribution to the coil 372 as illustrated in FIG. 5A when the electrical power is distributed. In this manner, the armature 374, the disk 375, and the plate 377 have predetermined intervals relative to each other in the rotation shaft direction. Since the both the hub 376 and the disk 375 rotate while the armature 374, the disk 375, and the plate 377 are not in contact with each other in a case in which the rotation shaft of the actuator 300 rotates, the disk 375 idles, and the brake force does not act on the rotation of the actuator 300. Note that the spring 379 that connects the base material 371 and the armature 374 is in a compressed state by the armature 374 being attracted by the base material 371 at this time.

FIG. 5B illustrates a condition of the brake mechanism 370 when no electrical power is distributed, that is, in a case in which the electrical power is not supplied to the coil 372. This corresponds to a state in which the rotation shaft of the actuator 300 is constrained by the brake mechanism 370.

Since the magnetic force caused by the electrical power distribution to the coil 372 is eliminated when the electrical power is not distributed, the armature 374 moves in the rotation shaft direction away from the base material 371 due to recovery force of the spring 379 as illustrated in FIG. 5B. In this manner, the disk 375 is pressurized by the plate 377 by the armature 374. Therefore, the rotation of the disk 375 is stopped, that is, the rotation of the rotation shaft of the actuator 300 is stopped by the stationary frictional force caused between the disk 375 and the plate 377.

Here, the brake force of the brake mechanism 370 is adjusted such that the weight of the arm 420 can be supported, the posture of the arm 420 can be held, and in a case in which external value that is equal to or greater than a predetermined value is loaded, the rotation shaft rotates in accordance with the external force when the electrical power is not distributed in the embodiment as described above. As described above, since the brake force of the brake mechanism 370 is stationary frictional force caused between the disk 375 and the plate 377, and the brake force of the brake mechanism 370 can be adjusted to satisfy the aforementioned conditions, by matters that can define magnitude of the stationary frictional force being adjusted in the embodiment.

For example, the brake force of the brake mechanism 370 can be adjusted by at least any of a contact area between the disk 375 and the plate 377, a stationary frictional coefficient of a contact surface between the disk 375 and the plate 377, and the recovery force of the spring 379 being adjusted.

Note that specifically, the brake force of the brake mechanism 370 may be decided such that the posture of the arm 420 can be held even at a worst posture at which the maximum stress in accordance with the weight of the arm 420 can act on the actuator 300 (that is, the joint portions 421a to 421f). It is possible to obtain the force acting on the actuator 300 at the worst posture can be obtained by performing simulation using a calculation model that imitates the structure of the arm 420. Specific design of the aforementioned respective configurations in the brake mechanism 370 can be performed such that the stationary frictional force (that is, the brake force) capable of standing the obtained force is realized.

In addition, the brake force of the brake mechanism 370 may be changed in accordance with the position at which the brake mechanism 370 is provided in the arm 420. For example, since the configurations to be supported at the joint portions 421a to 42f are lighter toward the tip end in the arm 420, the brake mechanism 370 of the actuator 300 provided on the tip end side requires less brake force than the brake mechanism 370 of the actuator 300 provided on the root side to hold the posture of the arm 420. Therefore, a difference may be provided in the brake force of the respective brake mechanisms 370 such that the brake force of the brake mechanism 370 of the actuator 300 becomes smaller toward the tip end side. In this manner, it is possible to finely design the brake force by adjusting the brake force for the respective brake mechanisms 370 and to thereby more appropriately realize behaviors of the arm 420 (stopping of the arm 420 and manual movement of the arm 420) when the electrical power is not distributed. Note that an optimal value of the brake force of the respective brake mechanisms 370 in accordance with the arrangement positions in the arm 420 may be obtained by repeatedly performing simulation in consideration of the aforementioned worst posture while providing a difference in the brake force.

The configuration of the brake mechanism 370 according to the embodiment has been described with reference to FIGS. 4 and 5. In the embodiment, the aforementioned brake mechanism 370 is mounted on each of the joint portions 421a to 421f of the arm device 400. As described above, the brake mechanism 370 is configured such that the joint portions 421a to 421f are fixed to hold the posture of the arm 420 in a case in which electrical power supply is stopped. Therefore, it is possible to safely stop the operations of the arm 420 even at the time of emergency such as interruption of electric supply. In addition, the brake force may be adjusted such that the joint portions 421a to 421f can operate in a case in which external force that is equal to or greater than a predetermined value acts. In this case, it is possible to manually cause the arm 420 to operate and to continue the surgery even if the power source is lost.

Further, it is determined that whether or not there is an abnormality in the arm 420 in a state in which the arm 420 is fixed by the brake mechanisms 370 in the embodiment as will be described in detail later. Therefore, it is possible to further improve safety of the arm device 400 according to the embodiment.

3. Configuration of Arm Control Device

Next, the configuration of the arm control device 430 will be described with reference to FIG. 6. The arm control device 430 includes a storage unit 431 and a control unit 432. Information necessary for operations of the arm control device 430, for example, programs and the like are stored in the storage unit 431. Further, an expected output value of the torque sensor 355 is calculated, and it is determined that whether or not there is an abnormality in the respective encoders and the torque sensor 355 on the basis of the expected output value and an actual output value from the torque sensor 355 in the embodiment, as will be described later. Therefore, information necessary to calculate the expected output value is also stored in the storage unit 431.

Here, the information necessary to calculate the expected output value is specifically structure parameters related to the structure of the arm 420. The storage unit 431 stores information that does not depend on the posture of the arm 420 from among the structure parameters. Specifically, the storage unit 431 stores the structure parameters related to the links 422a to 422d. Here, the dimensions, the gravity centers, the masses, and the like of the links 422a to 422d can be listed as the structure parameters related to the links 422a to 422d. Here, the link 422c is divided into a portion that is present between the joint portion 421c and the joint portion 421d and a portion that is present between the joint portion 421d and the joint portion 421e. In addition, the storage unit 431 also stores the structure parameters related to the imaging device 423. Here, the dimension, the gravity center, the mass, and the like of the imaging device 423 can be listed as the structure parameters related to the imaging device 423.

Note that structure parameters related to the joint portions 421a to 421f can be listed as the structure parameters that are affected by the posture of the arm 420. The rotating angles of the joint portions 421a to 421f can be listed as the structure parameters related to the joint portions 421a to 421f. The rotation angles of the joint portions 421a to 421f are measured by the output shaft encoder 340. Note that the rotation angles of the joint portions 421a to 421f are obtained by multiplying the value measured by the input shaft encoder 330 by a correction value. The correction value corresponds to a deceleration ratio of the decelerator 320.

In this manner, the structure parameters are parameters related to the joint portions 421a to 421f and the links 422a to 4224, for example. Other structure parameters can be present, and other structure parameters will be described later.

The control unit 432 performs the following processing in addition to the overall control of the arm 420 and the arm control device 430. That is, the control unit 432 activates the arm 420 in a case in which an activation command of the arm 420 is provided from the surgeon 520 or the like. Specifically, activation electrical power is supplied to the motors 310 of the respective actuators 300. However, the control unit 432 does not release the brake mechanisms 370. That is, the control unit 432 brings the brake mechanisms 370 into a state in which the electrical power is no distributed when the arm 420 is activated. In this manner, it is possible not to allow the arm 420 to perform an abnormal operation even in a case in which there is an abnormality in the arm 420. Further, the control unit 432 supplies drive electrical power to the imaging device 423. Here, the control unit 432 may stop the supply of the electrical power to the actuator 300 first and may continue the supply of the electrical power to the imaging device 423 as long as possible in a case in which an abnormality or malfunction has occurred in an electric system for the actuator 300 and the imaging device 423. In this manner, it is possible to continue the image capturing by the imaging device 423 even if an abnormality occurs in the arm 420. Therefore, the surgeon 520 can continue the surgery. Note that in a case in which the electrical power is not supplied to the actuator 300, the brake mechanisms 370 are brought into the state in which the electrical power is not distributed. That is, the brake mechanisms 370 can fix the arm 420. Therefore, the posture of the arm 420 is maintained.

Further, the control unit 432 determines whether or not there is an abnormality in the arm 420 in a state in which the arm 420 is fixed by the brake mechanism 370 when the arm 420 is activated. First, the control unit 432 calculates the expected output value of the torque sensor 355 for each of the joint portions. Specifically, the control unit 432 reads output values from the output shaft encoder 340 and the torque sensor 355 of each of the joint portions. Further, the control unit 432 reads the structure parameters from the storage unit 431. Then, the control unit 432 defines xyz axes in a space in which the arm 420 is present. For example, the rotation shaft of the joint portion 421a may be regarded as the z axis, and the rotation shaft of the joint portion 421b may be regarded as the x axis.

Further, the control unit 432 applies numerical values 1 to N (N is a total number of the joint portions; six in the example in FIG. 2) to the joint portions 421a to 421f. The numerical values decrease as the joint portions are closer to the tip end portion. Therefore, the numerical value applied to the joint portion 421f is "1", and the numerical value applied to the joint portion 421a is "6". Hereinafter, the joint portions with the numerical values "n" (n is any of the integers from 1 to N) will also be referred to as a joint portion "n". Also, the control unit 432 applies the numerical values 1 to N to the links or the imaging device connected directly on the tip end side of the joint portions 421a to 421f. For example, the numerical value that is applied to the link 422a is "6", and the numerical value applied to the imaging device 423 is "1". Hereinafter the link to which the numerical value "n" (n is any of integers 1 to N) will also be referred to as a link "n". The imaging device 423 corresponds to the link "1". In addition, the portion that is present between the joint portion 421c and the joint portion 421d corresponds to the link "4" while the portion that is present between the joint portion 421d and the joint portion 421e corresponds to the link "3". Then, the control unit 432 calculates the expected output value for each of the joint portions on the basis of Equations (1) to (10) below.

[Math. 1]

$$\tau_n = c'_n \times M'_n + l'_n \times F'_{n-1} + \tau'_{n-1} \quad (1)$$

In Equation (1). $\tau_n$ is an expected output value for the joint portion "n". In addition, $c'_n$, $l'_n$, $M'_n$, $F'_{n-1}$, and $\tau'_{n-1}$ are parameters represented by Equations (2) to (6) below.

[Math. 2]

$$c'_n = R(\theta_n) c_n \quad (2)$$

$$l'_n = R(\theta_n) l_n \quad (3)$$

$$M'_n = R(\theta_N) R(\theta_{N-1}) \ldots R(\theta_{n+1}) M_n \quad (4)$$

$$F'_{n-1} = \begin{cases} R(\theta_N) R(\theta_{N-1}) \ldots R(\theta_{n+1}) \sum_{i=1}^{n-1} M_i (n \geq 2) \\ 0 \quad (n = 1) \end{cases} \quad (5)$$

$$\tau'_{n-1} = \begin{cases} R(\theta_n)^{-1} \tau_{n-1} (n \geq 2) \\ 0 (n = 1) \end{cases} \quad (6)$$

Here, $R(\theta_n)$ in Equations (2) to (6) is a rotation matrix of the joint portion "n", and one of three rotation matrixes represented by Equation (7) below is selected in accordance with the rotation direction of the joint portion "n". $\theta_n$ is an output value provided from the output shaft encoder 340 corresponding to the joint portion "n". $c_n$ is a gravity center vector of the link "n" and is represented by Equation (8) below. $l_n$ is a tip end position vector (that is, a dimensional vector) of the link "n" and is represented by Equation (9) below. $M_n$ is a force vector by the mass of "n" and is represented Equation (10) below. Note that in a case in which the gravity direction is assumed to be a $-z$ direction, $M_x$ and $M_y$ are zero.

[Math. 3]

$$R(\theta_n) = \begin{cases} \begin{pmatrix} 1 & 0 & 0 \\ 0 & \cos\theta_n & -\sin\theta_n \\ 0 & \sin\theta_n & \cos\theta_n \end{pmatrix} \\ \begin{pmatrix} \cos\theta_n & 0 & \sin\theta_n \\ 0 & 1 & 0 \\ -\sin\theta_n & 0 & \cos\theta_n \end{pmatrix} \\ \begin{pmatrix} \cos\theta_n & -\sin\theta_n & 0 \\ \sin\theta_n & \cos\theta_n & 0 \\ 0 & 0 & 1 \end{pmatrix} \end{cases} \quad (7)$$

$$c_n = \begin{pmatrix} c_{n,x} \\ c_{n,y} \\ c_{n,z} \end{pmatrix} \quad (8)$$

$$l_n = \begin{pmatrix} l_{n,x} \\ l_{n,y} \\ l_{n,z} \end{pmatrix} \quad (9)$$

$$M_n = \begin{pmatrix} M_{n,x} \\ M_{n,y} \\ M_{n,z} \end{pmatrix} \quad (10)$$

Then, the control unit 432 determines whether or not there is an abnormality in the torque sensor 355 and the output shaft encoder 340 on the basis of the expected output value of the torque sensor 355 and the actual output value of the torque sensor 355 (that is, the output value read from the torque sensor 355). The control unit 432 performs the determination processing for each of the joint portions.

More specifically, the control unit 432 determines whether or not a difference between the expected output value of the torque sensor 355 and the actual output value of the torque sensor 355 is within a predetermined range. Then, in a case in which the deference therebetween is within the predetermined range, the control unit 432 determines that both the torque sensor 355 and the output shaft encoder 340 are normal. This is because the expected output value and the actual output value substantially coincide with each other if these sensors are normal. That is, the control unit 432 determines that the joint portion including the torque sensor 355 and the output shaft encoder 340 is normal. Note that it is expected that a slight difference is caused between the expected output value and the actual output value in many cases. Thus, the control unit 432 may perform calibration by using the difference as a correction value in a case in which the difference between the expected output value and the actual output value is within the predetermined range. In this manner, the control unit 432 can more stably and precisely perform the following abnormality determination. Note that a specific range of the predetermined range may be adjusted in accordance with safety or the like required by the arm 420. More priority is placed on the safety as the width of the predetermined range is narrower. Meanwhile, in a case in which the difference between the expected output value and the actual output value is outside the predetermined range, the control unit 432 determines that there is an abnormality in at least one of the torque sensor 355 and the output shaft encoder 340. This is because the expected output value and the actual output value are often large in a case in which there is an abnormality in at least one of the torque sensor 355 and the output shaft encoder 340. That is, the control unit 432 determines that there is an abnormality in the joint portion including the torque sensor 355 and the output shaft encoder 340.

Note that although the aforementioned determination is made by using the output value of the output shaft encoder 340 here, the aforementioned determination may be made by using the output value of the input shaft encoder 330. In this case, the output value of the input shaft encoder 330 may be corrected and then used. In this manner, it is possible to determine whether or not there is an abnormality in the torque sensor 355 and the input shaft encoder 330. The control unit 432 may perform both the determination processing using the output value of the output shaft encoder 340 and the determination processing using the output value of the input shaft encoder 330. In this manner, it is possible to determine whether or not there is an abnormality in the input shaft encoder 330, the output shaft encoder 340 and the torque sensor 355. In addition, although the expected output value may be calculated every time activation occurs, a value that is calculated in advance may be used. In the latter case, the following processing is performed, for example. That is, the control unit 432 returns the posture of the arm 420 to a predetermined initial posture to stop the arm 420. Then, the control unit 432 calculates the expected output value at the initial posture and causes the storage unit 431 to store the expected output value. Then, the control unit 432 reads the expected output value from the storage unit 431 when the arm 420 is activated. The following processing is similar to the aforementioned processing. That is, it is only necessary to compare the expected output value with the actual output value and to determine whether or not there is an abnormality.

In a case in which it is determined that there is no abnormality in all the joint portions 431a to 431f, the control unit 432 determines that there is no abnormality in the arm 420. Meanwhile, in a case in which there is an abnormality in any one of the joint portions 431a to 431f, the control unit 432 determines that there is an abnormality in the arm 420. The control unit 432 does not release the brake mechanisms 370 in a case in which it is determined that there is an abnormality in the arm 420. That is, the posture of the arm 420 is maintained. In this manner, the control unit 432 can more safely determine whether or not there is an abnormality in the arm 420 even in a case in which there is an abnormality in the arm 420. Therefore, in a case in which both the motor 310 and the sensor are out of order, or in a case in which only the sensor is out of order, the control unit 432 determines that there is an abnormality in the arm 420. In addition, the control unit 432 can further enhance safety of the arm 420, in particular, safety immediately after the arm 420 is activated since the control unit 432 does not release the brake mechanisms 370 in a case in which there is an abnormality in the arm 420.

Meanwhile, in a case in which it is determined that there is no abnormality in the arm 420 (that is, in a case in which it is determined that there is no abnormality in all the joint portions 431a to 431f), the control unit 432 releases the brake mechanism 370. Therefore, the brake mechanism 370 is released if the sensor is normal. Note that a case in which the sensor is normal while there is an abnormality in the motor 310 is assumed. However, the control unit 432 can immediately stop the arm 420 in a case in which the arm 420 is about to perform an abnormal operation since the sensor is normal. This is because an abnormal value is output from the sensor in this case.

The control unit 432 controls operations of the arm 420 after the brake mechanisms 370 are released. Note that force control is preferably used as a scheme for controlling the arm 420 in consideration of operability of the arm 420. Specifically, in a case in which the surgeon 520 touches directly the arm 420 and applies force thereto, the control unit 432 causes the arm 420 to move in a direction of the force applied to the arm 420. That is, the control unit 432 controls the motors 310 of the respective joint portions such that such movement is enabled. In this manner, the surgeon 520 can more intuitively operate the arm 420. It is a matter of course that the control unit 432 may cause the arm 420 to operate depending on another control scheme, for example, a control scheme such as position control. In a case in which the arm 420 operates by the position control, a controller is separately prepared.

In addition, the control unit 432 constantly monitors the output values from the sensors of the respective joint portions (that is, the input shaft encoder 320, the output shaft encoder 330, and the torque sensor 355) during the control of the operations of the arm 420. Then, in a case in which any of the output values appears as an abnormal value, the control unit 432 immediately stops the arm 420. Therefore, the control unit 432 can stop the arm 420 in a case in which the motor 310 of any of the joint portions is out of order, for example. Then, the control unit 432 brings the brake mechanism 370 into a state in which the electric poser is not distributed. In this manner, the control unit 432 maintains the posture of the arm 420. In this manner, safety of the arm 420 is further enhanced.

The control unit 432 may further perform the following processing. That is, the control unit 432 controls operations of the imaging device 423. Further, the control unit 432 displays an image provided from the imaging device 423 on the display device 550. Further, a notification device 600 may be connected to the arm control device 430. In this case, the control unit 432 may notify the surgeon 520 of a fact that there is an abnormality in the arm 420, by the notification device 600. The notification device 600 may be various sound output devices (for example, a speaker), light emitting devices (for example, a patrol lamp), or the like, for example. The display device 550 may also be used as the notification device 600. In this case, the control unit 432 may display the fact that there is an abnormality in the arm 420 on the display device 550. In addition, the control unit 432 may cause the arm 420 to vibrate by driving the actuator 300 in a case in which there is an abnormality in the arm 420.

The arm control device 430 can be configured of a processor such as a central processing unit (CPU) or a digital signal processor (DSP) or a microcomputer with such a processor mounted thereon. Then, the operations of the arm 420 are controlled by the processor executing signal processing in accordance with a predetermined program.

4. Abnormality Determination Processing Performed by Arm Control Device

Next, abnormality determination processing performed by the arm control device 430 will be described with reference to the flowchart illustrated in FIG. 7. In Step S10, the control unit 432 activates the arm 420 in a case in which an activation command of the arm 420 is provided from the surgeon 520 or the like. Specifically, the control unit 432 supplies drive power force to the motors 310 of the respective actuators 300. However, the control unit 432 does not release the brake mechanism 370. That is, the control unit 432 brings the brake mechanism 370 into a state in which the electrical power is not distributed when the arm 420 is activated. In this manner, it is possible not to allow the arm 420 to perform an abnormal operation even in a case in which there is an abnormality in the arm 420. Further, the control unit 432 supplies drive electrical power to the imaging device 423. The control unit 432 determines whether or not there is an abnormality in the arm 420 by the processing in and after Step S20 described below. That is, the control unit 432 determines whether or not there is an abnormality in the arm 420 in a state in which the arm 420 is fixed by the brake mechanisms 370.

In Step S20, output values are read from the output shaft encoders 340 at the respective joint portions and the torque sensors 355. In Step S30, the control unit 432 reads the structure parameter from the storage unit 431. In Step S40, the control unit 432 calculates the expected output value for each of the joint portions. Specific processing is as described above. Then, the control unit 432 performs processing in Steps S50 to S80 for each of the joint portions.

In Step S50, the control unit 432 calculates the difference between the expected output value of the torque sensor 355 and the actual output value of the torque sensor 355. In Step S60, the control unit 432 determines whether or not the difference between the expected output value of the torque sensor 355 and the actual output value of the torque sensor 355 is within the predetermined range. The control unit 432 moves on to Step S70 in a case in which the difference between the expected output value of the torque sensor 355 and the actual output value of the torque sensor 355 is within the predetermined range. In a case in which the difference between the expected output value of the torque sensor 355 and the actual output value of the torque sensor 355 is outside the predetermined range, the control unit 432 moves on to Step S80.

In Step S70, the control unit 432 determines whether or not both the torque sensor 355 and the output shaft encoder 340 are normal. That is, the control unit 432 determines that the joint portion including the torque sensor 355 and the output shaft encoder 340 is normal. In Step S80, the control unit 432 determines that there is an abnormality in at least one of the torque sensor 355 and the output shaft encoder 340. That is, the control unit 432 determines that there is an abnormality in the joint portion including the torque sensor 355 and the output shaft encoder 340. The control unit 432 performs Steps S50 to S80 on all the joint portions and then moves on to Step S90.

In a case in which it is determined that there is no abnormality in all the joint portions 431a to 431f in Step S90, the control unit 432 determines that there is no abnormality in the arm 420. Meanwhile, in a case in which there is an abnormality in any one of the joint portions 431a to 431f, the control unit 432 determines that there is an abnormality in the arm 420. In a case in which it is determined that there is an abnormality in the arm 420, the control unit 432 does not release the brake mechanisms 370. That is, the posture of the arm 420 is maintained. In this manner, the control unit 432 can further safely determine whether or not there is an abnormality in the arm 420 even in a case in which there is abnormality in the arm 420. Meanwhile, in a case in which it is determined that there is no abnormality in the arm 420 (that is, in a case in which it is determined that there is no abnormality in all the joint portions 431a to 431f), the control unit 432 releases the brake mechanism 370. Therefore, the brake mechanism 370 is released if the sensor is normal. Note that a case in which the sensor is normal while there is an abnormality in the motor 310 is assumed. However, the control unit 432 can immediately stop the arm 420 in a case in which the arm 420 is about to perform an abnormal operation since the sensor is normal. This is because an abnormal value is output from the sensor in this case.

5. Modification Examples of Abnormality Determination Processing

Next, modification examples of the abnormality determination processing performed by the arm control device 430 will be described on the basis of FIGS. 8 to 12. Note that the arm 420 is illustrated in a simplified manner in FIGS. 8 to 12. Note that the link 422c is represented separately as links 422c-1 and 422c-2. The link 422c-1 is a portion that couples the joint portion 421c to the joint portion 421d, and the link 422c-2 is a portion that couple the joint portion 421d to the joint portion 421e.

Figure 8:
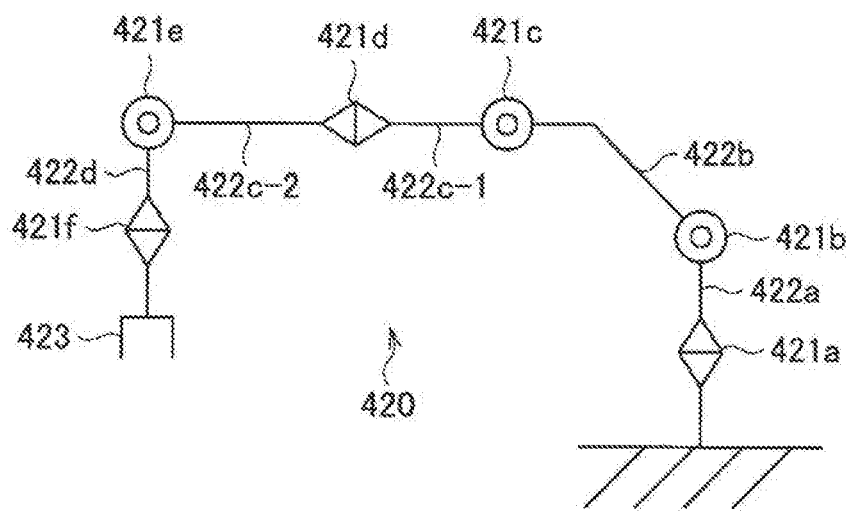
FIG. 8 is a conceptual diagram illustrating a modification example of the processing according to the embodiment.

In a first modification example illustrated in FIG. 8, the link 422b is deformed. In this case, the difference between the expected output value and the actual output value is large since the actual output value of the torque sensor 355 greatly varies. Therefore, the control unit 432 can determine that there is an abnormality in the arm 420. That is, the control unit 432 can determined that there is an abnormality in the arm 420 in a case in which any of the links is deformed.

Figure 9:
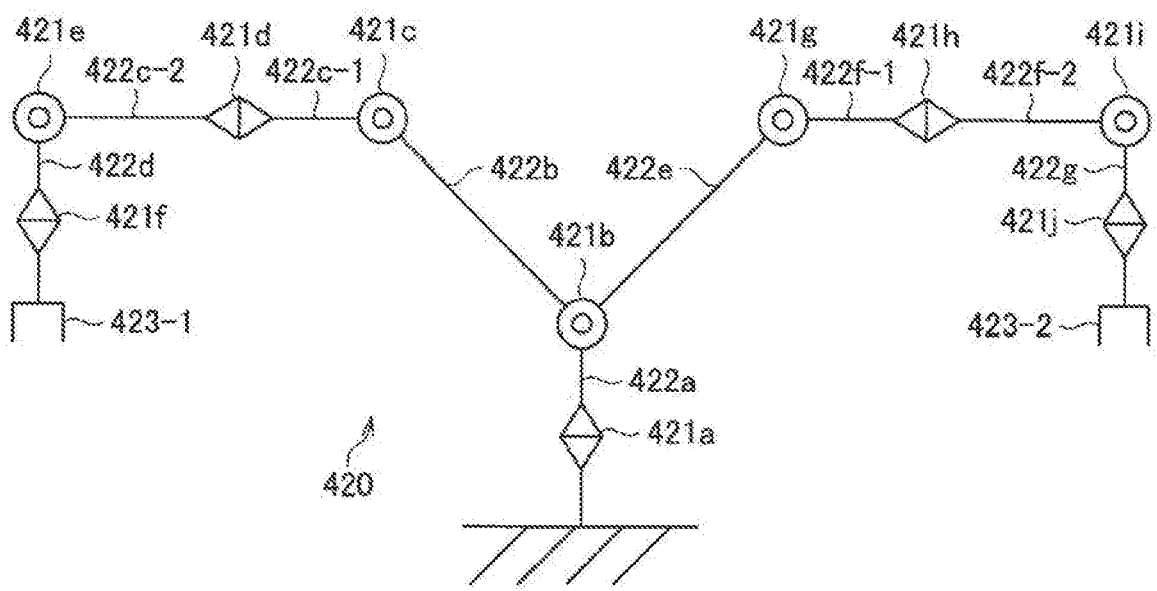
FIG. 9 is a conceptual diagram illustrating a modification example of the processing according to the embodiment.

In the second modification example illustrated in FIG. 9, the arm 420 is branched into two parts at the joint portion 421b. That is, the arm 420 has joint portions 421a to 421j, links 422a to 422g, and imaging devices 423-1 and 423-2. In such a case, the abnormality determination processing itself may be the same although the number of the structure parameters increases. That is, the control unit 432 can determine whether or not there is an abnormality in the arm 420 even in a case in which the arm 420 is branched. Note that in this case, different devices may be attached to the respective arms.

Figure 10:
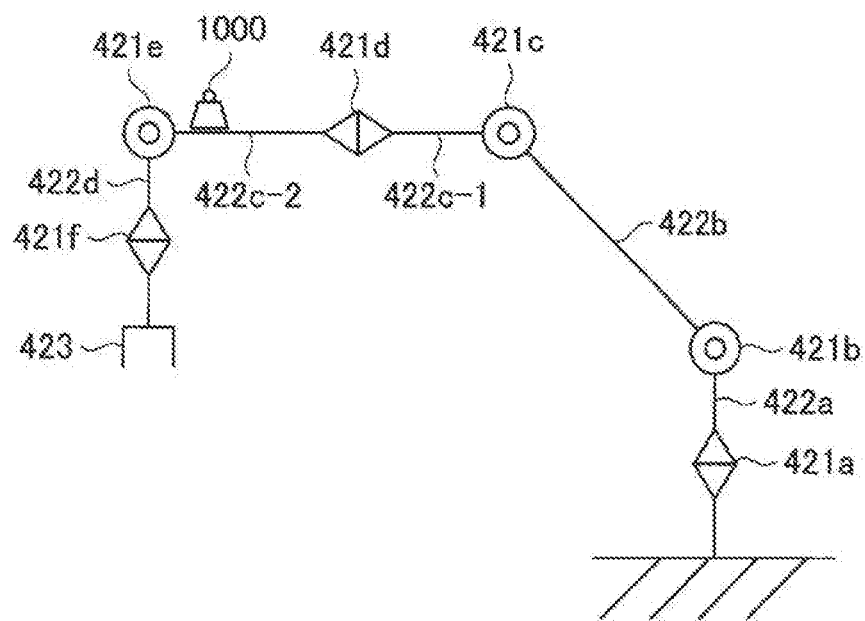
FIG. 10 is a conceptual diagram illustrating a modification example of the processing according to the embodiment.

In the third modification example illustrated in FIG. 10, excessive loads 1000 are provided at the tip end of the link 422c-2. The excessive loads 100 may be heavy objects in some cases or become loads applied by the surgeon 520 or the like to the links 422c-2. In this case, since the actual output value of the torque sensor 355 greatly varies, the difference between the expected output value and the actual output value becomes large. Therefore, the control unit 432 can determine that there is an abnormality in the arm 420. That is, in a case in which the excessive loads are applied to a part of the arm 420, the control unit 432 can determine that there is an abnormality in the arm 420. Note that there is a case in which heavy objects are attached to the tip ends of the arm 420 depending on purposes of the arm 420. For example, the arm 420 is used for a medical purpose, various kinds of medical equipment are attached to the tip end of the arm 420. The heavy objects are also included in these pieces of medical equipment. For example, a significantly heavy imaging device 423 is also present as the imaging device 423 illustrated as an example in the embodiment. Therefore, a threshold value (the predetermined range in Step S50) with which the difference between the expected output value and the actual output value is compared may be alleviated depending on the purpose of the arm 420. That is, the predetermined range may be widened.

Figure 11:
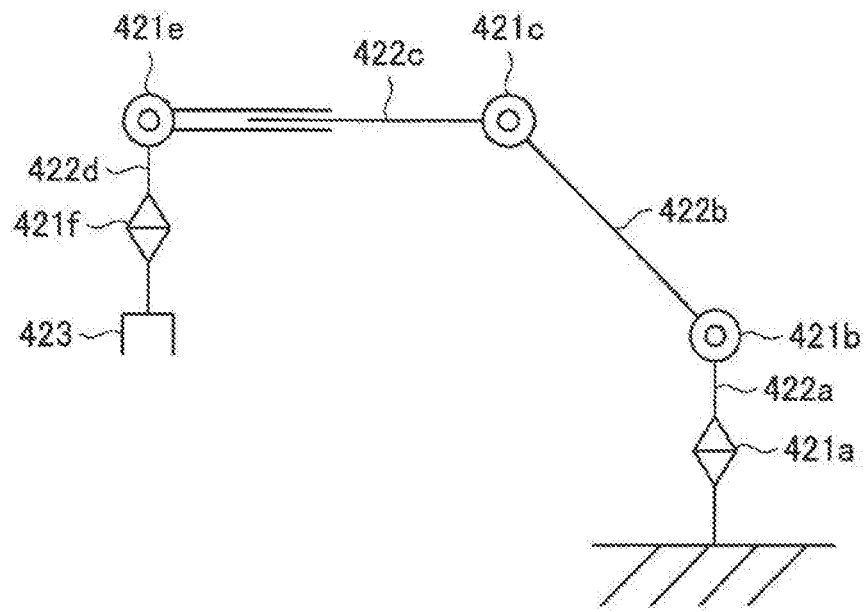
FIG. 11 is a conceptual diagram illustrating a modification example of the processing according to the embodiment.

In a fourth modification example illustrated in FIG. 11, the link 422c is freely extended and contracted. That is, the link 422c has an actuator, which is not illustrated in the drawing, and the link 422c is freely extended and contracted by the actuator. The control unit 432 also performs the control of the actuator. In addition, the control unit 432 calculates the dimension and the gravity center of the link 422c on the basis of the amount of displacement of the link 422c. The other processing may be similar to the aforementioned normality determination processing. Therefore, the control unit 432 can determine whether or not there is an abnormality in the arm 420 even in a case in which the link that is freely extended and contracted is included in the arm 420.

Figure 12:
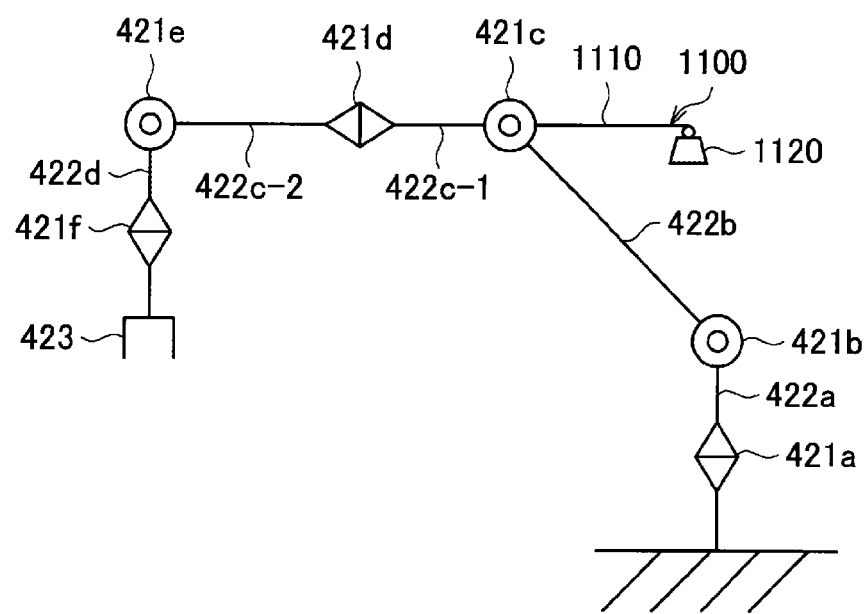
FIG. 12 is a conceptual diagram illustrating a modification example of the processing according to the embodiment.

In a fifth modification example illustrated in FIG. 12, a counterweight 1100 is provided at the joint portion 421c. The counterweight 1100 includes a link 1110 that extends from the joint portion 421c and a heavy object 1120 that is provided at the tip end of the link 1110. In this case, the control unit 432 calculates the expected output value of the torque sensor 355 for the link "n" (the link "4" in the example illustrated in FIG. 12), on the basis of Equation (11) below.

[Math. 4]

$$\tau_n = c'_n \times M'_n + l'_n \times F'_{n-1} + \tau'_{n-1} + \tau_{counter_n} \quad (11)$$

In Equation (11), $\tau_{counter\ n}$ is a parameter represented by Equation (12) below.

[Math. 5]

$$\tau_{counter_n} = l'_{counter_n} \times M'_{counter_n} \quad (12)$$

Further, $l'_{counter_n}$ and $M'_{counter_n}$ are parameters represented by Equations (13) and (14) below.

[Math. 6]

$$l'_{counter_n} = R(\theta_n) l_{counter_n} \quad (13)$$

$$M'_{counter_n} = R(\theta_N) R(\theta_{N-1}) \ldots R(\theta_{n+1}) M_{counter_n} \quad (14)$$

Here, $l_{counter\ n}$ is a gravity center position vector of the counterweight 1100, and $M_{counter\ n}$ is a force vector due to the weight of the counterweight 1100.

Note that in a case in which the counterweight 1100 is a so-called spring-type counterweight, the gravity center position vector and the force vector of the counterweight 1100 are defined by the amount of deformation and the force point of the spring.

In addition, in a case in which a property that a spring mechanism is non-linear (for example, correspondence between elastic force of the spring and the displacement are non-linear or the like) is present, the control unit 432 may perform calibration in advance by using the property. In this manner, accuracy of the expected output value of the torque sensor 355 can be improved.

That is, in a case in which there is a counterweight 1100, the control unit 432 may calculate the expected output value of the torque sensor 355 by using a scheme of referring to a value measured in advance alone or in combination. The "alone" described here means that the expected output value itself is calculated in advance as described above. In addition, "in combination" means that a part of data (for example, the non-linear property of the spring mechanism) used to calculate the expected output value is calculated in advance.

In addition, in a case in which a complete balance has been achieved by the counterweight 1100, the aforementioned processing may not be performed since the output value of the torque sensor 355 does not vary.

In addition, the control unit 432 may perform all the processing in the aforementioned modification examples or may perform a part of the processing.

According to the embodiment, the arm control device 430 can determine whether or not there is an abnormality in the arm 420 in a state in which the arm 420 is fixed by the brake mechanisms 370 as described above. Therefore, the arm control device 430 can more safely determine whether or not there is an abnormality in the arm 420.

In addition, the arm control device 430 determines whether or not there is an abnormality in the arm 420 when the arm 420 is activated. Therefore, it is possible by the arm control device 430 not to allow the arm 420 to perform an abnormal operation when the arm 420 is activated.

Further, the arm control device 430 determines whether or not there is an abnormality in the sensor (for example, the input shaft encoder 330, the output shaft encoder 340, and the torque sensor 355) provided at the joint portions 421a to 421f of the arm 420. Therefore, the arm control device 430 can more reliably determine whether or not there is an abnormality in the arm 420.

Further, the sensor (for example, the torque sensor 355) can detect a state (for example, an external torque) of the arm 420 when the arm 420 is fixed by the brake mechanisms 370. Then, the arm control device 430 determines whether or not there is an abnormality in the sensor on the basis of the output values from the sensor. Therefore, the arm control device 430 can more reliably determine whether or not there is an abnormality in the arm 420.

Further, the arm control device 430 determines whether or not there is an abnormality in the sensor on the basis of the structure parameters related to the structure of the arm 420 and can thus more reliably determine whether or not there is an abnormality in the arm 420.

Further, the arm control device 430 calculates the expected output value of the sensor on the basis of the structure parameters and determines whether or not there is an abnormality in the sensor on the basis of the expected output values of the sensor and the actual output values of the sensor. Therefore, the arm control device 430 can more reliably determine whether or not there is an abnormality in the arm 420.

Further, the arm control device 430 determines that there is no abnormality in the sensor in a case in which the difference between the expected output value of the sensor and the actual output value of the sensor is a value within the predetermined range. Therefore, the arm control device 430 can more reliably determine whether or not there is an abnormality in the arm 420.

Further, the arm control device 430 performs calibration by using the difference between the expected output value of the sensor and the actual output value of the sensor as the correction value. Therefore, the arm control device 430 can more reliably and accurately determine whether or not there is an abnormality in the arm 420.

Further, since the parameters related to the joint portions 421a to 421f are included in the structure parameters, the arm control device 430 can more reliably determine whether or not there is an abnormality in the arm 420.

Further, since the rotation angles of the joint portions 421a to 421f are included in the structure parameters, the arm control device 430 can more reliably determine whether or not there is an abnormality in the arm 420.

Further, since the parameters related to the links 422a to 422d that couple the joint portions 421a to 421f are included in the structure parameters, the arm control device 430 can more reliably determine whether or not there is an abnormality in the arm 420.

Further, at least one or more kinds from among the dimensions of the links 422a to 422d, the gravity centers of the links 422a to 422d, and the masses of the links 422a to 422d are included in the structure parameters. Therefore, the arm control device 430 can more reliably determine whether or not there is an abnormality in the arm 420.

Further, in a case in which the counterweight 1100 is coupled to any of the joint portions 421a to 421f, the parameters related to the counterweight 1100 are included in the structure parameters. Therefore, the arm control device 430 can more reliably determine whether or not there is an abnormality in the arm 420.

Further, at least one kind from among the torque sensor 355, the input shaft encoder 330, and the output shaft encoder 340 is included in the sensors that are targets of determination about whether or not there is an abnormality. Therefore, the arm control device 430 can more reliably determine whether or not there is an abnormality in the arm 420.

Further, the arm control device 430 releases the brake mechanism 370 in a case in which it is determined that there is no abnormality in the arm 420. Therefore, the arm control device 430 can more safely start the activation of the arm 420.

Further, since the arm 420 is adapted for a medical purpose, persons such as the surgeon 520 and the patient 540 can be present in the surroundings. That is, the arm 420 is required to have high safety. In such a case, the arm control device 430 can more reliably determine whether or not there is an abnormality in the arm 420.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Although the arm 420 is an arm for holding a surgery device in the aforementioned embodiment, for example, the arm 420 may be applied to another arm, such as a surgery master-slave system used in remote surgery, or to any technical fields other than the medical field such as arms for industries and arms for polar regions.

Further, the effects described in this specification are merely illustrative or exemplified effects, and are not limitative. That is, with or in the place of the above effects, the technology according to the present disclosure may achieve other effects that are clear to those skilled in the art from the description of this specification. Additionally, the present technology may also be configured as below.

(1)
An arm control method including:
determining, using a processor, whether or not there is an abnormality in an arm that operates by being driven by an actuator in a state in which the arm is fixed by a brake mechanism.

(2)
The arm control method according to (1), in which the processor determines whether or not there is an abnormality in the arm when the arm is activated.

(3)
The arm control method according to (1) or (2), in which the processor determines whether or not there is an abnormality in a sensor that is provided at a joint portion of the arm.

(4)
The arm control method according to (3),
in which the sensor is able to detect a state of the arm when the arm is fixed by the brake mechanism, and the processor determines whether or not there is an abnormality in the sensor on a basis of an output value of the sensor.

(5)
The arm control method according to (4), in which the processor determines whether or not there is an abnormality in the sensor on a basis of a structure parameter related to a structure of the arm.

(6)
The arm control method according to (5), in which the processor calculates an expected output value of the sensor on a basis of the structure parameter and determines whether or not there is an abnormality in the sensor on a basis of the expected output value of the sensor and an actual output value of the sensor.

(7)
The arm control method according to (6), in which the processor determines that there is no abnormality in the sensor in a case in which a difference between the expected output value of the sensor and the actual output value of the sensor is a value within a predetermined range.

(8)
The arm control method according to (7), in which the processor performs calibration by using the difference between the expected output value of the sensor and the actual output value of the sensor as a correction value.

(9)
The arm control method according to any one of (5) to (8), in which a parameter related to the joint portion is included in the structure parameter.

(10)
The arm control method according to (9), in which a rotation angle of the joint portion is included in the structure parameter.

(11)
The arm control method according to any one of (5) to (10), in which a parameter related to a link that couples the joint portions is included in the structure parameter.

(12)
The arm control method according to (11), in which at least one or more of a dimension of the link, a center of gravity of the link, and a mass of the link are included in the structure parameter.

(13)
The arm control method according to any one of (5) to (12), in which in a case in which a counterweight is coupled to the joint portion, a parameter related to the counterweight is included in the structure parameter.

(14)
The arm control method according to any one of (4) to (13), in which at least one of a torque sensor that detects a torque that acts on an output shaft of the joint portion and a rotation angle sensor that detects a rotation angle of the joint portion is included in the sensor.

(15)
The arm control method according to any one of (1) to (14), in which the processor releases the brake mechanism in a case in which it is determined that there is no abnormality in the arm.

(16)
The arm control method according to (15), in which the processor performs control such that the actuator is caused to be driven in a case in which it is determined that there is no abnormality in the arm.

(17)
The arm control method according to any one of (1) to (16), in which the arm is for a medical purpose.

(18)
An arm control device including:
a control unit that determines whether or not there is an abnormality in an arm that operates by being driven by an actuator in a state in which the arm is fixed by a brake mechanism.

REFERENCE SIGNS LIST 300 actuator
310 motor
320 decelerator
330 input shaft encoder
340 output shaft encoder
350 output shaft
355 torque sensor
370 brake mechanism
400 arm device
420 arm
421a to 421f joint portion
422a to 422d link
430 arm control device
431 storage unit
432 control unit

The invention claimed is:

1. A surgery arm system comprising:
a multiple-joint arm that has a plurality of joints coupled by a plurality of links such that the joints are configured to turn and a tip end to which an imaging device configured to observe a surgical site is configured to be coupled; and
processing circuitry configured to control the multiple-joint arm such that a position and a posture of the imaging device are changed, wherein
the processing circuitry is further configured to
control electric power supply to the actuator and the imaging device,
determine whether or not there is an abnormality in sensors provided at the joints when the multiple-joint arm is activated after electric power supply to a brake is cut off, in a state in which the multiple-joint arm that operates by being driven by an actuator provided at least one of the plurality of joints is fixed by the brake, and
in a case in which the abnormality in the sensors is detected, stop the electric power supply to the actuator and continue the electric power supply to the imaging device.

2. The surgery arm system according to claim 1, wherein the sensors are configured to detect a state of the multiple-joint arm when the multiple-joint arm is fixed by the brake, and
the processing circuitry is configured to determine whether or not there is the abnormality in the sensors on a basis of output values of the sensors.

3. The surgery arm system according to claim 2, wherein the processing circuitry is configured to determine whether or not there is the abnormality in the sensors on a basis of structure parameters related to a structure of the multiple-joint arm.

4. The surgery arm system according to claim 3, wherein the processing circuitry is configured to calculate expected output values of the sensors on a basis of the structure parameters and determines whether or not there is the abnormality in the sensors on a basis of the expected output values of the sensors and actual output values of the sensors.

5. The surgery arm system according to claim 4, wherein the processing circuitry is configured to determine that there is no abnormality in the sensor in a case in which a difference between the expected output value of the sensor and the actual output value of the sensor is a value within a predetermined range.

6. The surgery arm system according to claim 5, wherein the processing circuitry is configured to perform calibration by using the differences between the expected output values of the sensors and the actual output values of the sensors as correction values.

7. The surgery arm system according to claim 3, wherein parameters related to the joints are included in the structure parameters.

8. The surgery arm system according to claim 7, wherein rotation angles of the joints are included in the structure parameters.

9. The surgery arm system according to claim 3, wherein a parameter related to a link that couples the joints is included in the structure parameters.

10. The surgery arm system according to claim 9, wherein at least one or more of a dimension of the link, a center of gravity of the link, and a mass of the link are included in the structure parameters.

11. The surgery arm system according to claim 3, wherein in a case in which a counterweight is coupled to the joint, a parameter related to the counterweight is included in the structure parameters.

12. The surgery arm system according to claim 2, wherein at least one of a torque sensor that detects torque that acts on an output shaft of the joint and a rotation angle sensor that detects a rotation angle of the joint is included in the sensor.

13. The surgery arm system according to claim 1, wherein the processing circuitry is configured to release the brake in a case in which it is determined that there is no abnormality in the multiple-joint arm.

14. The surgery arm system according to claim 13, wherein the processing circuitry is configured to perform control such that the actuator is caused to be driven in a case in which it is determined that there is no abnormality in the multiple-joint arm.

15. The surgery arm system according to claim 1, wherein brake force caused by the brake is adjusted such that a rotation shaft of the actuator is able to be rotated by external force that is equal to or greater than a predetermined value while electric power supply is cut off.

* * * * *